United States Patent
Mereddy et al.

(10) Patent No.: US 9,296,728 B2
(45) Date of Patent: Mar. 29, 2016

(54) THERAPEUTIC COMPOUNDS

(71) Applicant: Regents of the University of Minnesota, Minneapolis, MN (US)

(72) Inventors: Venkatram R. Mereddy, Minneapolis, MN (US); Lester R. Drewes, Minneapolis, MN (US); Mohammed Abrar Alam, Minneapolis, MN (US); Sravan K. Jonnalagadda, Minneapolis, MN (US); Shirisha Gurrapu, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/373,615

(22) PCT Filed: Jan. 18, 2013

(86) PCT No.: PCT/US2013/022275
§ 371 (c)(1),
(2) Date: Jul. 21, 2014

(87) PCT Pub. No.: WO2013/109972
PCT Pub. Date: Jul. 25, 2013

(65) Prior Publication Data
US 2014/0371272 A1    Dec. 18, 2014

Related U.S. Application Data

(60) Provisional application No. 61/589,090, filed on Jan. 20, 2012.

(51) Int. Cl.
| | | |
|---|---|---|
| C07D 311/02 | (2006.01) | |
| C07D 405/04 | (2006.01) | |
| C07D 407/14 | (2006.01) | |
| C07C 255/41 | (2006.01) | |
| C07D 295/155 | (2006.01) | |
| C07C 255/63 | (2006.01) | |
| C07D 207/09 | (2006.01) | |
| C07D 311/12 | (2006.01) | |

(52) U.S. Cl.
CPC ............ *C07D 405/04* (2013.01); *C07C 255/41* (2013.01); *C07C 255/63* (2013.01); *C07D 207/09* (2013.01); *C07D 295/155* (2013.01); *C07D 311/12* (2013.01); *C07D 407/14* (2013.01)

(58) Field of Classification Search
CPC .................................................... C07C 255/41
USPC ........................................................ 549/287
See application file for complete search history.

(56) References Cited

U.S. PATENT DOCUMENTS

| | | | |
|---|---|---|---|
| 4,317,774 A | 3/1982 | Sassiver et al. | |
| 5,043,243 A | 8/1991 | Yajima et al. | |
| 7,141,735 B2 * | 11/2006 | Ikeda et al. | ................... 136/263 |
| 2006/0024525 A1 | 2/2006 | Jeong et al. | |

FOREIGN PATENT DOCUMENTS

| | | | | |
|---|---|---|---|---|
| CN | 101055328 A | | 10/2007 | |
| GB | 684386 | | 12/1952 | |
| JP | 45030069 | * | 2/1967 | |
| JP | 63286843 A | * | 11/1988 | ............... G03C 1/72 |
| JP | 10-204085 A | | 8/1998 | |
| JP | 2006-106675 | | 4/2006 | |
| JP | 2007-286189 | * | 11/2007 | ............... G02B 5/22 |
| WO | WO 02/11213 A1 | | 2/2002 | |
| WO | WO 03/074519 A1 | | 9/2003 | |
| WO | WO 2004/065394 A1 | | 8/2004 | |
| WO | WO 2009/109499 A1 | | 9/2009 | |
| WO | WO 2010/089580 A1 | | 8/2010 | |

OTHER PUBLICATIONS

Michel et al. Prostaglandins (1984), 27(1), 69-84.*
Teng et al. Chemistry—A European Journal (2010), 16(44), 13127-13138.*
Kakio et al. The Journal of biological chemistry (2001), 276(27), 24985-90.*
Artico et al. Annali di Chimica (Rome, Italy) (1966), 56(174-81), 1-2.*
Katz et al Journal of the American Chemical Society (1989), 111(19), 7554-7.*
Harishkumar Organic Communications (2011), 4(2), 26-32.*
Walker, Journal of the American Chemical Society (1958), 80, 645-52.*
Nandy et al. Organic Letters (2007), 9(12), 2249-2252.*
Smith, Journal of Organic Chemistry (1949), 14, 740-46.*
Besson et al., "Synthesis and Fluorescent Properties of some Heterobifunctional and Rigidized 7-Aminocoumarins", *J. Heterocyclic Chem.* 28, 1517-1523 (1991).
Bueno et al., "The specific monocarboxylate transporter (MCT1) inhibitor, AR-C117977, a novel immunosuppressant, prolongs allograft survival in the mouse", *Transplantation* 84 (9), 1204-1207 (2007).
Cho et al., "Mechanism analysis of long-term graft survival by monocarboxylate transporter-1 inhibition", *Transplantation* 90 (12), 1299-1306 (2010).

(Continued)

*Primary Examiner* — Nizal Chandrakumar
(74) *Attorney, Agent, or Firm* — Viksnins Harris & Padys PLLP

(57) ABSTRACT

The invention provides compounds of formula (I) or a salt thereof as described herein. The invention also provides pharmaceutical compositions comprising a compound of formula (I), processes for preparing compounds of formula (I), intermediates useful for preparing compounds of formula (I) and therapeutic methods for treating cancer or treating autoimmune diseases or preventing transplant rejection using compounds of formula (I).

7 Claims, 6 Drawing Sheets

(56) References Cited

OTHER PUBLICATIONS

Database Registry [Online], Chemical Abstracts Service, XP002699947, Accession No. 1095853-58-9 Abstract, 1 page, (2009).

Database WPI, Week 199041 Thomason Scientific, XP002699948, AN 1990-309545 & JP H02219692A (1990).

Drewes, "Signaling Regulation of Monocarboxylate Transporter-1 in Brain Vascular Endothelial Cells", 14th Symposium on Signal Transduction in the Blood Brain Barriers, Istanbul, Turkey, 26 pages, Sep. 8, 2011.

Ekberg et al., "The specific monocarboxylate transporter-1 (MCT-1) inhibitor, AR-C117977, induces donor-specific suppression, reducing acute and chronic allograft rejection in the rat", *Transplantation* 84 (2), 1191-1199 (2007).

Fujino et al., "Synthesis and Reactivity of 7-Dimethylaminocoumarin-3-carbonyl Fluoride as a Fluorescent Derivatization Reagent for Amines", Yakugaku Zasshi 110 (9), 693-696 (1990). [English Abstract Only].

Gazit et al., "Tyrphostins I: Synthesis and Biological Activity of Protein Tyrosine Kinase Inhibitors", *J. Med. Chem.* 32 (10), 2344-2352 (1989).

Hao, et al., "Co-expression of CD147 (EMMPRIN), CD44v3-10, MDR1 and monocarboxylate transporters is associated with prostate cancer drug resistance and progression", *Br J Cancer* 103 (7), 1008-1018 (2010).

Mathupala et al., "Silencing of monocarboxylate transporters via small interfering ribonucleic acid inhibits glycolysis and induces cell death in malignant glioma: an in vitro study", *Neurosurgery* 55 (6), 1410-1419 (2004).

Murray et al., "Monocarboxylate transporter MCT1 is a target for immunosuppression", *Nat Chem Biol* 1 (7), 371-376 (2005).

Nitsche et al., "Arylcyanoacrylamides as inhibitors of the Dengue and West Nile virus proteases", *Bioorg. Med. Chem.* 19, 7318-7337 (2011).

Patent Cooperation Treaty, International Searching Authority, Search Report and Written Opinion for PCT/US2013/022275, 17 pages, Jul. 18, 2013.

Popp, "Synthesis of potential anti-cancer agents. Part I. Benzaldehyde "Nitrogen Mustard" in the Knoevenagel Reaction", *Journal of the Chemical Society*, 5271-2, XP-002699945, (1960).

Rozhkov et al., "Fluorogenic Transformations Based on Formation of C—C Bonds Catalyzed by Palladium: An Efficient Approach for High Throughput Optimizations and Kinetic Studies", *Adv. Synth. Catal.*, 350, 71-75 (2008).

Scifinder Search for (E)-2-cyano-3-(4-(dipropylamino)phenyl)acrylic acid, Scifinder, 1 page, 2011.

Scifinder Search for (E)-2-cyano-3-(4-(diphenylamino)phenyl)acrylic acid, Scifinder, 13 pages, 2011.

Scifinder Search for 7-(diphenylamino)-2-oxo-2H-chromene-3-carboxylic acid, Scifinder, 2 pages, 2011.

Scifinder Search for (E)-2-cyano-3-(4-(dimethylamino)phenyl)acrylic acid, Scifinder, 22 pages, 2011.

Scifinder Search for 7-(dimethylamino)-2-oxo-2H-chromene-3-carboxylic acid, Scifinder, 3 pages, 2011.

Scifinder Search for (E)-2-cyano-3-(4-(diethylamino)phenyl)acrylic acid, Scifinder, 2 pages, 2011.

Scifinder Search for 7-(diethylamino)-2-oxo-2H-chromene-3-carboxylic acid, Scifinder, 103 pages, 2011.

Scifinder Search of Bischloroethylamine, Scifinder, 1 page, 2011.

Scifinder Search of 7-(dibutylamino)-2-oxo-2H-chromene-3-carboxylic acid, Scifinder, 1 page, 2011.

Scifinder Search of (E)-2-cyano-3-(4-(diethylamino)-2-methoxyphenyl)acrylic acid, Scifinder, 1 page, 2011.

Secci et al., "Synthesis and selective human monoamine oxidase inhibition of 3-carbonyl, 3-acyl, and 3-carboxyhydrazido coumarin derivatives", *European Journal of Medicinal Chemistry* 46, 4846-4852 (2011).

Sonveaux et al., "Targeting lactate-fueled respiration selectively kills hypoxic tumor cells in mice", *J. Clin. Invest.*, 118 (12), 3930-3942 (2008).

Su et al., "A CD147-targeting siRNA inhibits the proliferation, invasiveness, and VEGF production of human malignant melanoma cells by down-regulating glycolysis" *Cancer Letters*, vol. 273 (1), 140-147 (2009).

Teng et al., "Tuning the HOMO Energy Levels of Organic Dyes for Dye-Sensitized Solar Cells Based on Br/Br3 Electrolytes", *Chem. Eur. J.* 16, 13127-13138, (2010).

* cited by examiner

THERAPEUTIC COMPOUNDS

RELATED APPLICATIONS

This application claims priority to U.S. Provisional Application No. 61/589,090 that was filed on 20 Jan. 2012.

BACKGROUND OF THE INVENTION

Monocarboxylate Transporters (MCTs) are members of the solute carrier 16 (SLC16) gene family. In mammalian species there are 14 known MCT isoforms and only four (MCT-1, -2, -3, -4) have been demonstrated to perform proton-linked transport of monocarboxylates such as lactate, pyruvate, butyrate, and ketone bodies.

Malignant tumors contain aerobic and hypoxic regions and intratumoral hypoxia increases the risk of cancer advancement, and metastasis. Tumor hypoxia leads to treatment failure, relapse and patient mortality as these cells are generally resistant to standard chemo- and radiation therapy. In regions of hypoxia, cancer cells metabolize glucose into lactate, whereas nearby aerobic cancer cells take up this lactate via the mono-carboxylate transporter 1 (MCT1) for oxidative phosphorylation. MCT1 expression is elevated in an array of human tumors including brain, breast, head, neck, lung and colon.

Under hypoxic conditions, cancer cells upregulate glucose transporters and consume large quantities of glucose. Cancer cells also upregulate glycolytic enzymes and convert glucose into lactate, which is then effluxed out of the cell via MCT4. The nearby aerobic cancer cells take up this lactate via the MCT1 for energy generation through oxidative phosphorylation. Thus, the limited glucose available to the tumor is used most efficiently via a synergistic metabolic symbiosis. This utilization of lactate as an energy substitute for survival prevents the aerobic cells from consuming large quantities of glucose. Targeted inhibition of MCT4 will lead to lactic acidosis and consequent death of hypoxic cells, while MCT1 inhibition will cause aerobic cancer cells to consume glucose instead of lactate, thus resulting in further stress and death of hypoxic cancer cells.

The inhibition of MCT1 may also be useful for treating autoimmune diseases and preventing organ transplant rejection. The rate of short term graft survival has been improved by current immunosuppressants, however in the past two decades there has been no improvement in the abilities of agents to promote long term graft survival. Recently it has been demonstrated that agents which inhibit MCT1 have been shown to aid prolonged allograft survival, prevent chronic rejection, and induce tolerance in rat allograft models. In an immune response, a rapid division of T cells occurs, and these activated T cells use glycolysis as their means for energy production. Interestingly, the activated T cells use glycolysis even though the cells exist in an aerobic environment. As MCT1 plays a critical role in the aerobic glycolysis of the activated T cells by exporting lactate, inhibition of MCT1 leads to a buildup of lactate in the cell. This in turn decreases glycolytic flux effectively limiting the proliferation of new lymphocytes.

There is a current need for agents that are useful for treating or preventing cancer or that are useful for treating or preventing autoimmune diseases or that are useful for preventing transplant rejection. There is also a need for agents that are useful for diagnosing cancer or autoimmune diseases or for imaging cancerous cells or cells involved in an autoimmune response.

SUMMARY OF THE INVENTION

In one embodiment, the invention provides a compound of the invention which is a compound of formula I:

wherein:

X is CN, Y is $R^5$ and the dashed bond is absent; or

X is —C(=O)—, Y is O and the dashed bond is a single bond;

$R^1$ is H or $(C_1$-$C_6)$alkyl;

$R^2$ is H, $(C_1$-$C_6)$alkyl, $(C_1$-$C_6)$alkoxy, halo$(C_1$-$C_6)$alkyl, halo, —OH, —CN, —$NO_2$, —$CO_2R_a$, —C(=O)$R_a$, —$NR_a$(C=O)$R_b$, —C(=O)$NR_cR_d$ or —$NR_cR_d$;

$R^3$ is H, $(C_1$-$C_6)$alkyl, $(C_1$-$C_6)$alkoxy, halo$(C_1$-$C_6)$alkyl, halo, —OH, —CN, —$NO_2$, —$CO_2R_a$, —C(=O)$R_a$, —$NR_a$(C=O)$R_b$, —C(=O)$NR_cR_d$ or —$NR_cR_d$;

$R^4$ is H, $(C_1$-$C_6)$alkyl, $(C_1$-$C_6)$alkoxy, halo$(C_1$-$C_6)$alkyl, halo, —OH, —CN, —$NO_2$, —$CO_2R_a$, —C(=O)$R_a$, —$NR_a$(C=O)$R_b$, —C(=O)$NR_cR_d$ or —$NR_cR_d$;

$R^5$ is H, $(C_1$-$C_6)$alkyl, $(C_1$-$C_6)$alkoxy, halo$(C_1$-$C_6)$alkyl, halo, —OH, —CN, —$NO_2$, —$CO_2R_a$, —C(=O)$R_a$, —$NR_a$(C=O)$R_b$, —C(=O)$NR_cR_d$ or —$NR_cR_d$;

$R^{6a}$ and $R^{6b}$ are each independently H, $(C_1$-$C_7)$alkyl, $(C_2$-$C_7)$alkenyl, $(C_2$-$C_7)$alkynyl, aryl$(C_1$-$C_6)$alkyl-, heteroaryl$(C_1$-$C_6)$alkyl-, heterocycle$(C_1$-$C_6)$alkyl-, aryl, heterocycle or heteroaryl, wherein any $(C_1$-$C_7)$alkyl, $(C_2$-$C_7)$alkenyl, $(C_2$-$C_7)$alkynyl, aryl$(C_1$-$C_6)$alkyl-, heteroaryl$(C_1$-$C_6)$alkyl-, heterocycle$(C_1$-$C_6)$alkyl-, aryl, heterocycle or heteroaryl of $R^{6a}$ and $R^{6b}$ is optionally substituted with one or more (e.g. 1, 2, 3, 4 or 5) $Z^1$ groups; or $R^{6a}$ and $R^{6b}$ together with the nitrogen to which they are attached form a heterocycle, wherein the heterocycle is optionally substituted with one or more (e.g. 1, 2, 3, 4 or 5) $Z^1$ groups;

each $R_a$ is independently H, $(C_1$-$C_6)$alkyl, aryl$(C_1$-$C_6)$alkyl- or aryl;

each $R_b$ is independently $(C_1$-$C_6)$alkyl, aryl$(C_1$-$C_6)$alkyl- or aryl;

$R_c$ and $R_d$ are each independently H, $(C_1$-$C_6)$alkyl, aryl$(C_1$-$C_6)$alkyl- or aryl; or $R_c$ and $R_d$ together with the nitrogen to which they are attached form a pyrrolidino, piperidino, piperazino, azetidino, morpholino, or thiomorpholino;

each $Z^1$ is independently $(C_1$-$C_6)$alkyl, $(C_1$-$C_6)$alkoxy, halo$(C_1$-$C_6)$alkyl, halo, —OH, —CN, —$NO_2$, —$CO_2R_e$, —C(=O)$R_e$, —$NR_e$(C=O)$R_f$, —C(=O)$NR_gR_h$ or —$NR_gR_h$;

each $R_e$ is independently H, $(C_1$-$C_6)$alkyl, aryl$(C_1$-$C_6)$alkyl- or aryl;

each $R_f$ is independently $(C_1$-$C_6)$alkyl, aryl$(C_1$-$C_6)$alkyl- or aryl; and $R_g$ and $R_h$ are each independently H, $(C_1$-$C_6)$alkyl, aryl$(C_1$-$C_6)$alkyl- or aryl; or $R_g$ and $R_h$ together with the nitrogen to which they are attached form a pyrrolidino, piperidino, piperazino, azetidino, morpholino, or thiomorpholino;

or a salt thereof.

The invention also provides a pharmaceutical composition comprising a compound of formula I, or a pharmaceutically acceptable salt thereof, and a pharmaceutically acceptable diluent or carrier.

The invention also provides a method for inhibiting cancer (e.g. lung, breast, brain, prostate, pancreatic, colorectal, ovarian, head and neck) cell growth comprising contacting the cancer cell in vitro or in vivo with an effective amount of a compound of formula I, or a salt thereof.

The invention also provides a method for treating cancer (e.g. lung, breast, brain, prostate, pancreatic, colorectal, ovarian, head and neck cancer) in a mammal (e.g. a human) comprising administering to the mammal an effective amount of compound as described in formula I, or a pharmaceutically acceptable salt thereof.

The invention also provides a method for treating an autoimmune disease (e.g. rheumatoid arthritis) in a mammal (e.g. a human) comprising administering to the mammal an effective amount of a compound of formula I, or a pharmaceutically acceptable salt thereof.

The invention also provides a method for preventing transplant rejection (e.g. heart, kidney, eye, liver, lung, pancreas, intestine, and thymus transplant rejection) or tissue graft rejection (e.g. bone, tendon, cornea, skin, heart valve and vein) in a mammal (e.g. a human) comprising administering to the mammal an effective amount of a compound of formula I, or a pharmaceutically acceptable salt thereof.

The invention also provides a method for diagnosing cancer (e.g. lung, breast, brain, prostate, pancreatic, colorectal, ovarian, head and neck cancer) or for diagnosing an autoimmune disease (e.g. rheumatoid arthritis) in a mammal comprising administering to the mammal (e.g. a human) an effective amount of a compound of formula I, or a pharmaceutically acceptable salt thereof and measuring or imaging the fluorescence of the compound of formula I wherein the fluorescence correlates with cancer or an autoimmune disease.

The invention also provides a method for imaging cancerous cells (e.g. brain, breast, head, neck, lung or colon cancer cells) or for imaging cells involved in an autoimmune response (e.g. rheumatoid arthritis) or for imaging cells involved in transplant rejection (e.g. heart, kidney, eye, liver, lung, pancreas, intestine, and thymus transplant rejection) or tissue graft rejection (e.g. bone, tendon, cornea, skin, heart valve and vein) comprising contacting the cells in vivo or in vitro with a compound of formula I, or a salt thereof and imaging the fluorescence of the compound of formula I while in contact with the cell.

The invention also provides a method for altering brain function (e.g. long-term memory formation) in a mammal (e.g. a human) comprising administering to the mammal an effective amount of a compound of formula I, or a pharmaceutically acceptable salt thereof.

The invention also provides a compound of formula I, or a pharmaceutically acceptable salt thereof, for use in medical therapy.

The invention also provides the use of a compound of formula I, or a pharmaceutically acceptable salt thereof, for the manufacture of a medicament useful for the treatment of cancer (e.g. lung, breast, brain, prostate, pancreatic, colorectal, ovarian, and head and neck cancer) in a mammal (e.g. a human).

The invention also provides a compound of formula I, or a pharmaceutically acceptable salt thereof, for use in the prophylactic or therapeutic treatment of cancer (e.g. lung, breast, brain, prostate, pancreatic, colorectal, ovarian, head and neck cancer).

The invention also provides a compound of formula I, or a pharmaceutically acceptable salt thereof, for use in the prophylactic or therapeutic alteration of brain function The invention also provides the use of a compound of formula I, or a pharmaceutically acceptable salt thereof, for the manufacture of a medicament useful for the treatment of an autoimmune disease (e.g. rheumatoid arthritis) in a mammal (e.g. a human).

The invention also provides the use of a compound of formula I, or a pharmaceutically acceptable salt thereof, for the manufacture of a medicament useful for altering brain function (e.g. long-term memory formation) in a mammal (e.g. a human).

The invention also provides a compound of formula I, or a pharmaceutically acceptable salt thereof, for use in the prophylactic or therapeutic treatment of an autoimmune disease (e.g. rheumatoid arthritis).

The invention also provides the use of a compound of formula I, or a pharmaceutically acceptable salt thereof, for the manufacture of a medicament useful for preventing transplant rejection (e.g. heart, kidney, eye, liver, lung, pancreas, intestine, and thymus transplant rejection) or tissue graft rejection (e.g. bone, tendon, cornea, skin, heart valve and vein) in a mammal (e.g. a human).

The invention also provides a compound of formula I, or a pharmaceutically acceptable salt thereof, for use in the prevention of transplant rejection (e.g. heart, kidney, eye, liver, lung, pancreas, intestine, and thymus transplant rejection) or tissue graft rejection (e.g. bone, tendon, cornea, skin, heart valve and vein).

The invention also provides a compound of formula I, or a salt thereof for use in diagnosing cancer (e.g. lung, breast, brain, prostate, pancreatic, colorectal, ovarian, head and neck) or for diagnosing a autoimmune disease (e.g. rheumatoid arthritis).

The invention also provides a compound of formula I, or a salt thereof for use in imaging cancerous cells (e.g. brain, breast, head, neck, lung or colon cancer cells) or for imaging cells involved in an autoimmune response (e.g. rheumatoid arthritis) or for imaging cells involved in transplant rejection (e.g. heart, kidney, eye, liver, lung, pancreas, intestine, and thymus transplant rejection) or tissue graft rejection (e.g. bone, tendon, cornea, skin, heart valve and vein).

The invention also provides processes and intermediates disclosed herein that are useful for preparing compounds of formula I or salts thereof.

DETAILED DESCRIPTION

Figure 1:
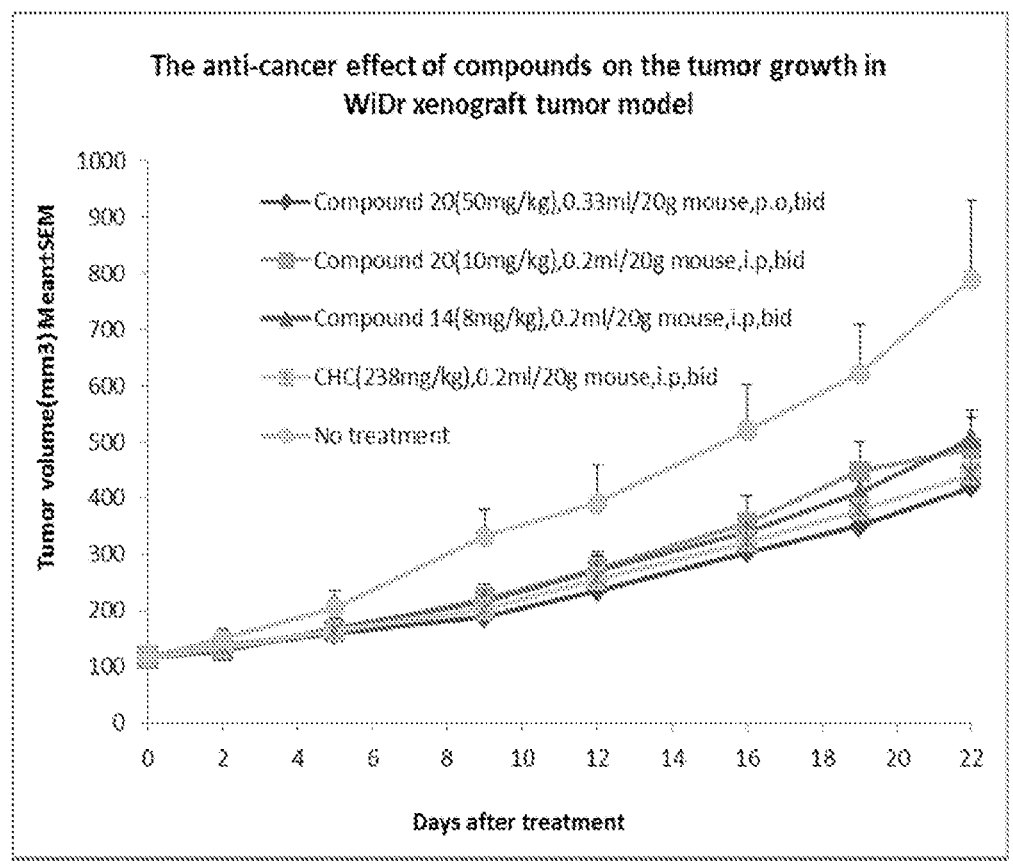
FIG. 1 illustrates the anti-cancer effect of Compound 20, and Compound 14 on the tumor growth in WiDr xenograft tumor model from Example 7.

The following definitions are used, unless otherwise described.

The term "halo" or "halogen" as used herein refers to fluoro, chloro, bromo, or iodo.

The term "alkyl" as used herein refers to straight and branched hydrocarbon groups; the term "alkenyl" as used herein refers to straight or branched hydrocarbon groups containing at least one carbon-carbon double bond; the term "alkynyl" as used herein refers to straight or branched hydrocarbon groups containing at least one carbon-carbon triple bond; the term "alkoxy" as used herein refers to groups of the formula alkyl-O—, where alkyl is as defined herein. Reference to an individual radical such as propyl embraces only the straight chain radical, a branched chain isomer such as isopropyl being specifically referred to.

The term "haloalkyl" as used herein refers to an alkyl as defined herein, wherein one or more hydrogen atoms are each replaced by a halo substituent. For example, a halo($C_1$-$C_6$) alkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1,2,3,4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen).

Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "carbocycle" or "carbocyclyl" refers to a single saturated (i.e., cycloalkyl) or a single partially unsaturated (e.g., cycloalkenyl, cycloalkadienyl, etc.) ring having 3 to 8 carbon atoms (i.e. ($C_3$-$C_8$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, spiro[4.5]decane, etc), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

When trade names are used herein, applicants intend to independently include the tradename product and the active pharmaceutical ingredient(s) of the tradename product.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents.

A specific group of compounds of formula I are compounds of formula Ia:

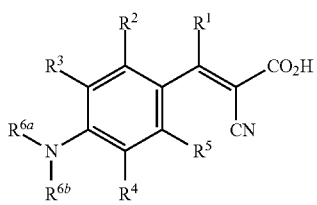

or a salt thereof.

A specific group of compounds of formula I are compounds of formula Ib:

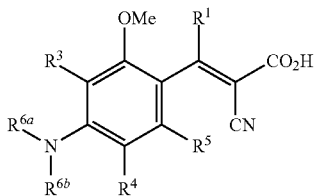

or a salt thereof.

Another specific group of compounds of formula I are compounds of formula Ic:

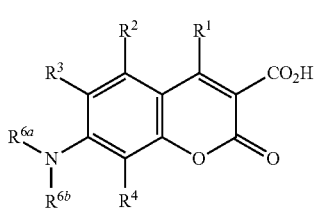

or a salt thereof.

Specific values listed below are values for compounds of formula I as well as all sub-formulas of formula I (e.g. formulas Ia, Ib, Ic, 1b, 2b and 3b).

Specifically, $(C_1-C_6)$alkyl can be methyl, ethyl, propyl, isopropyl, butyl, iso-butyl, sec-butyl, pentyl, 3-pentyl or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; and halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl.

A specific value for $R^1$ is H.

A specific value for $R^2$ is H or methoxy.

Another specific value for $R^2$ is methoxy.

Another specific value for $R^2$ is H.

A specific value for $R^3$ is H.

A specific value for each of $R^{6a}$ and $R^{6b}$ independently is $(C_1-C_6)$alkyl, $(C_2-C_6)$alkenyl, $(C_2-C_6)$alkynyl, aryl$(C_1-C_6)$alkyl-, aryl or heterocycle, wherein any $(C_1-C_6)$alkyl, $(C_2-C_6)$alkenyl, $(C_2-C_6)$alkynyl, aryl$(C_1-C_6)$alkyl-, aryl or heterocycle of $R^{6a}$ and $R^{6b}$ is optionally substituted with one or more $Z^1$ groups; or $R^{6a}$ and $R^{6b}$ together with the nitrogen to which they are attached form a heterocycle optionally substituted with one or more $Z^1$ groups.

Another specific independent value for each of $R^{6a}$ and $R^{6b}$ independently is $(C_1-C_6)$alkyl, aryl$(C_1-C_6)$alkyl- or aryl, wherein any $(C_1-C_6)$alkyl, aryl$(C_1-C_6)$alkyl- or aryl of $R^{6a}$ and $R^{6b}$ is optionally substituted with one or more $Z^1$ groups.

A specific value for —$NR^{6a}R^{6b}$ is:

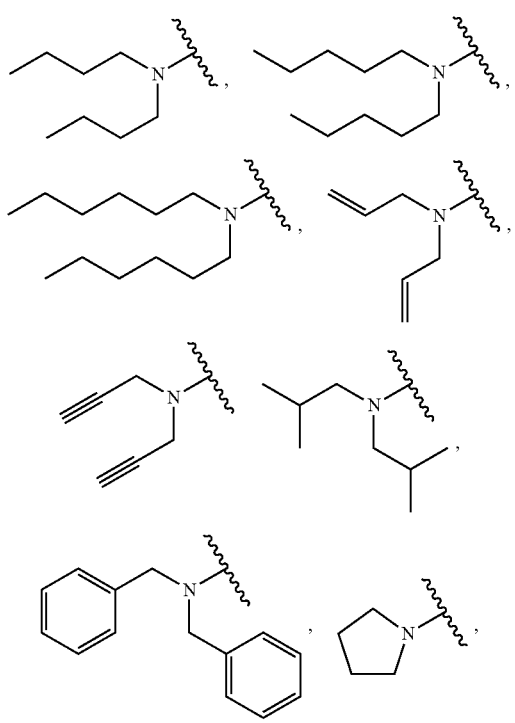

-continued
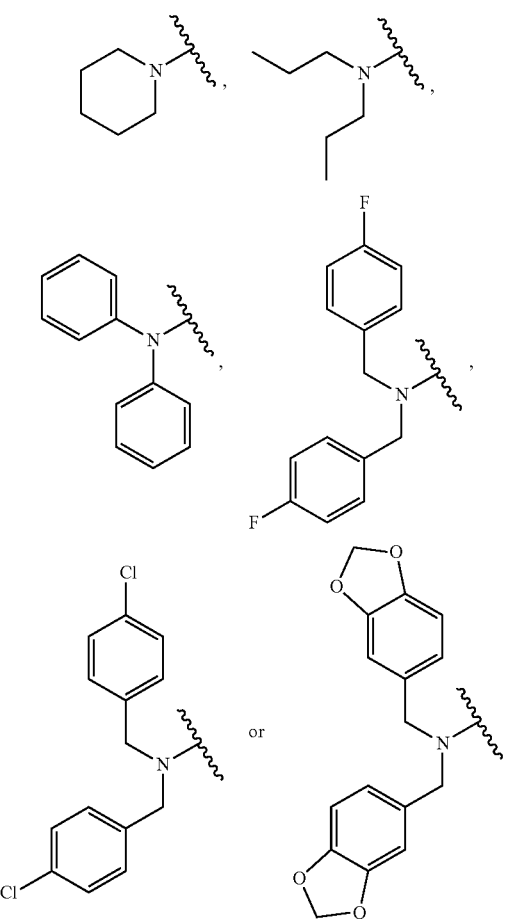
Another specific value for —NR$^{6a}$R$^{6b}$ is:
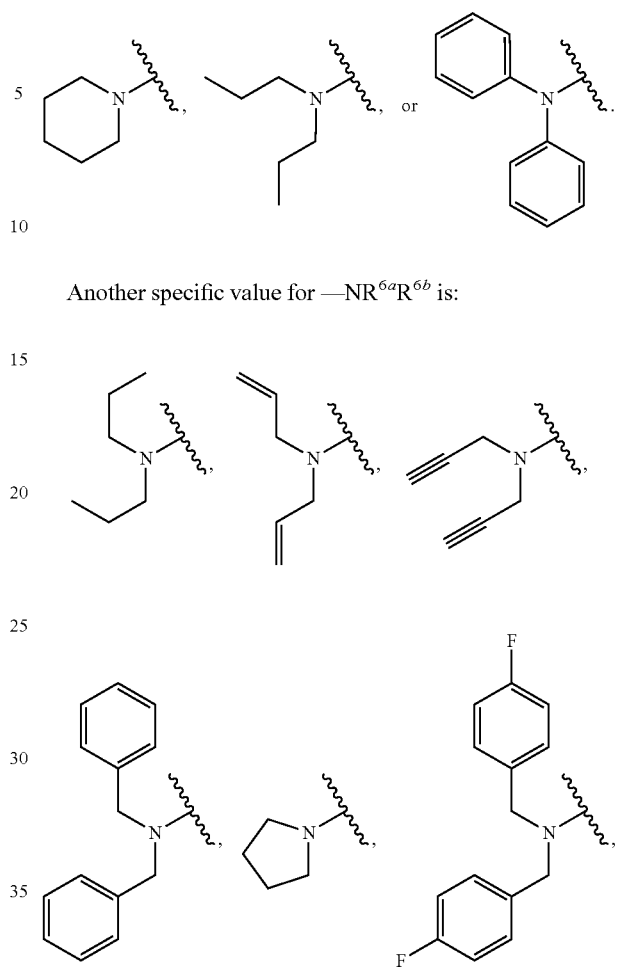
Another specific value for —NR$^{6a}$R$^{6b}$ is:

-continued
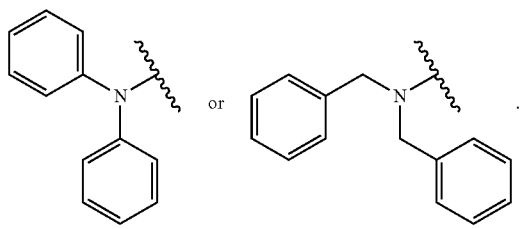 or .
A specific compound of formula I is:
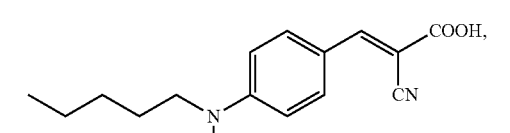
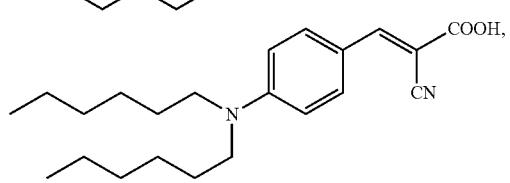
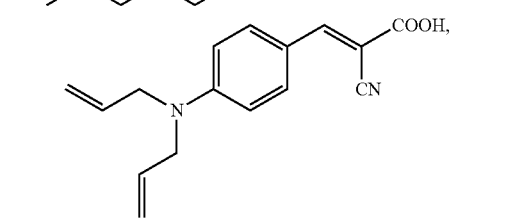
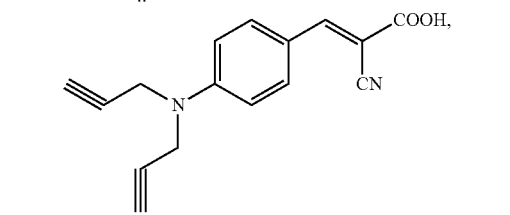
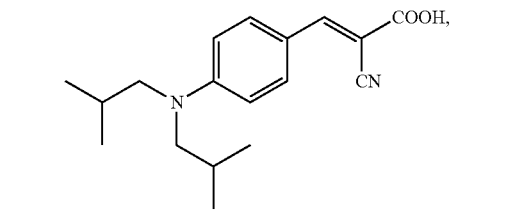
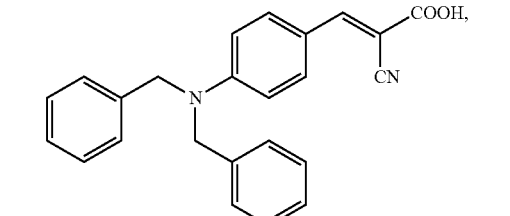
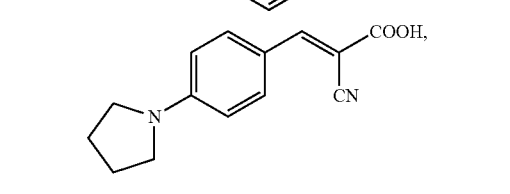
-continued
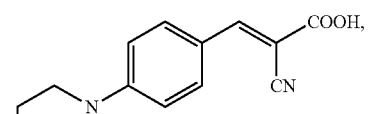
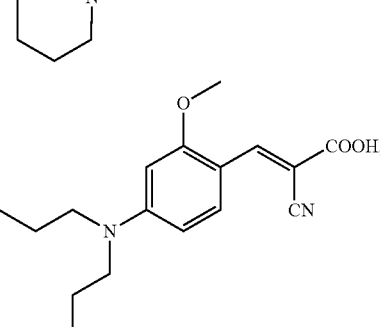
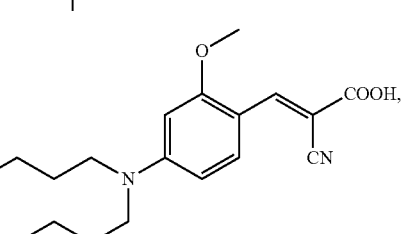
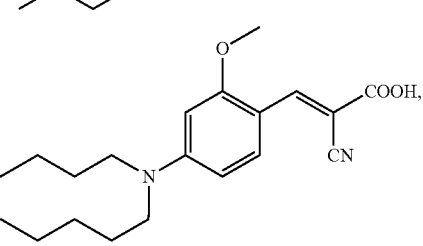
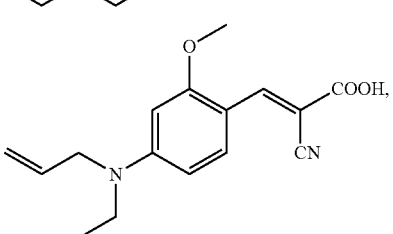
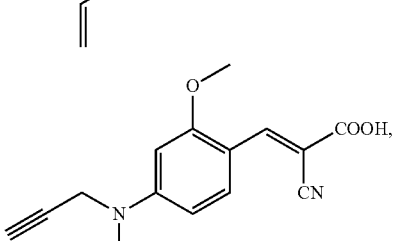
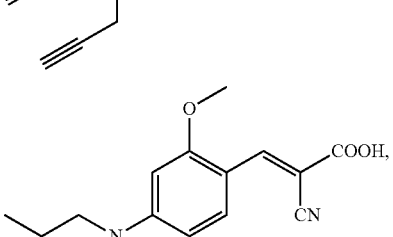
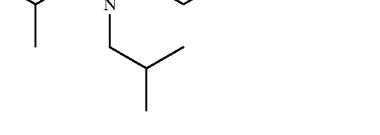

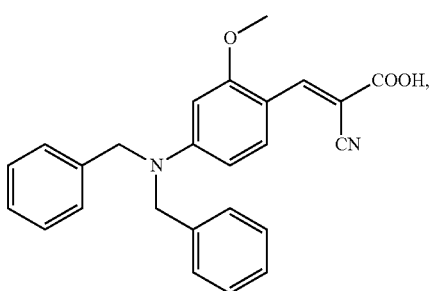
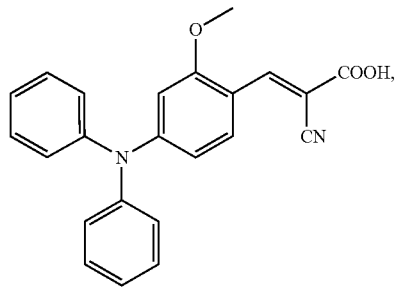
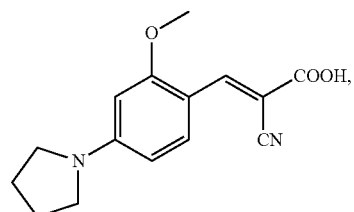
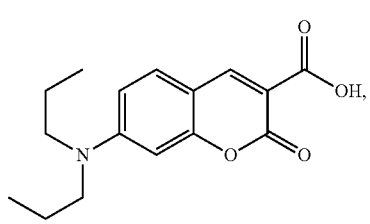
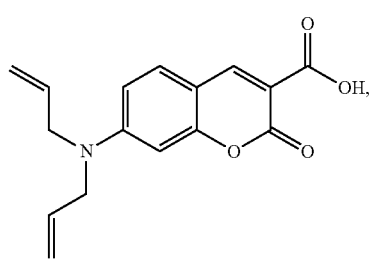
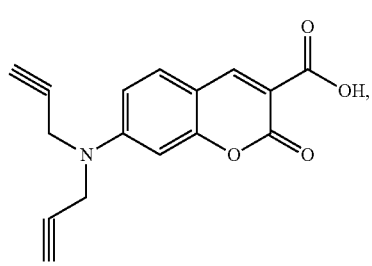
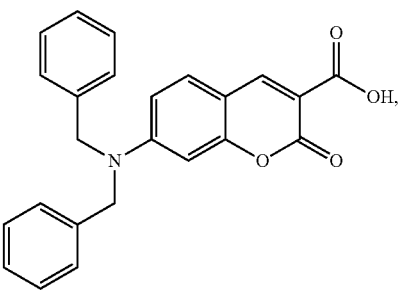
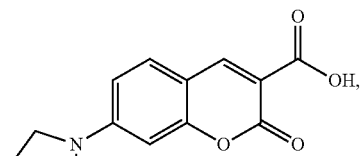
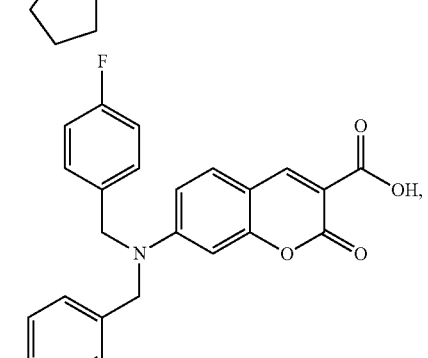
or
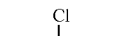
or a salt thereof.

A specific compound of formula I is:
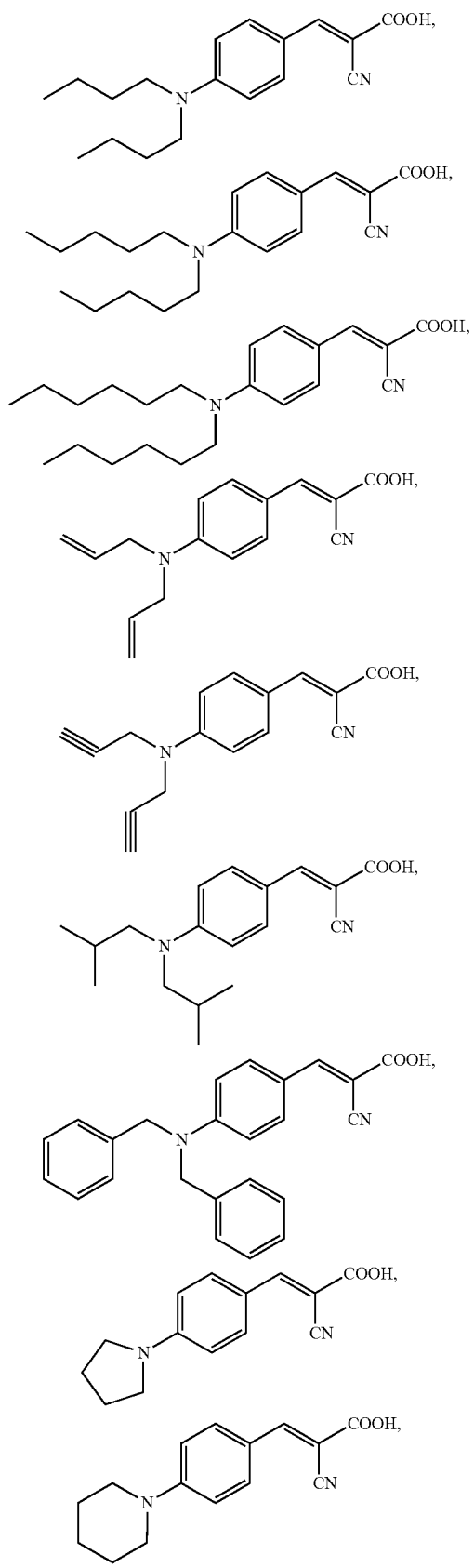
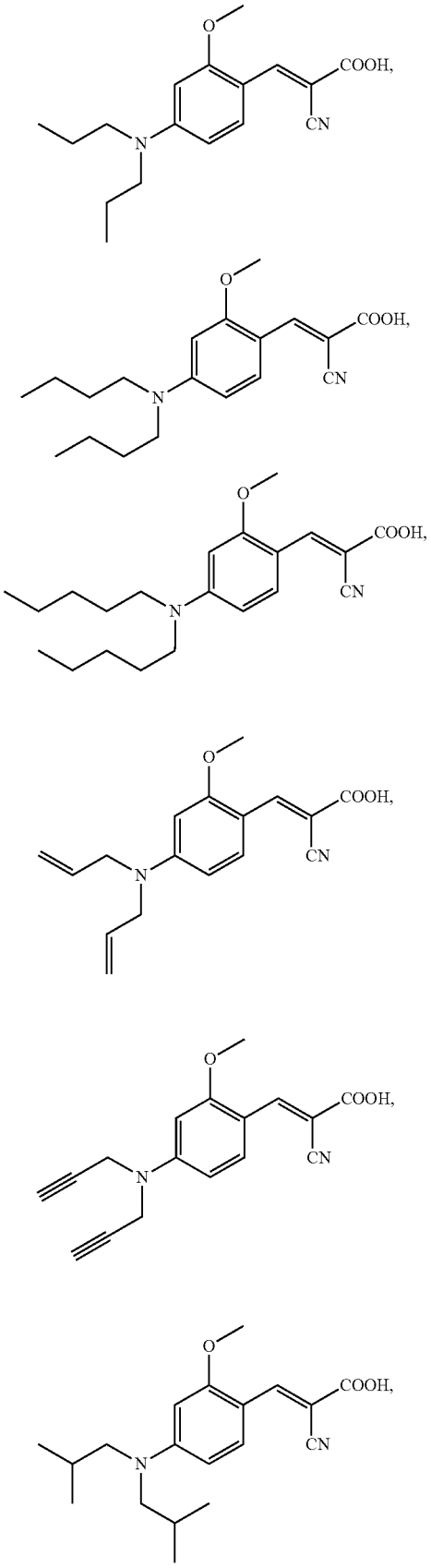
-continued

-continued
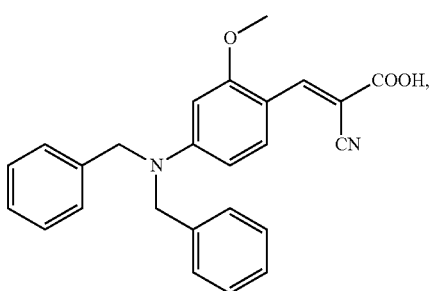
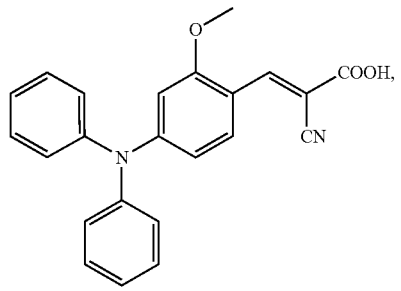
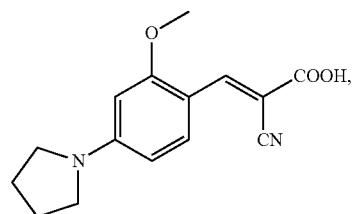
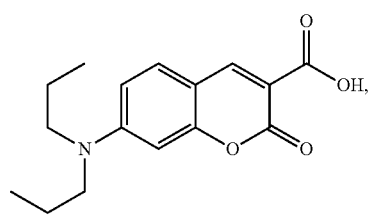
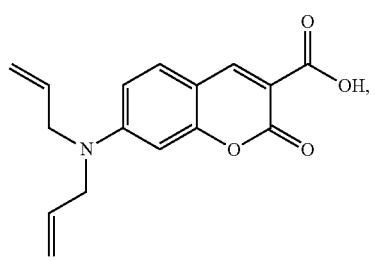
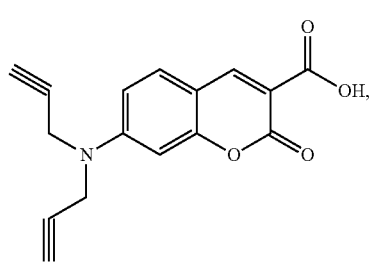
-continued
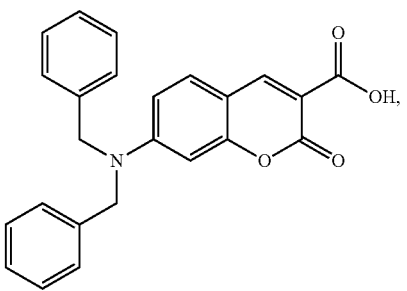
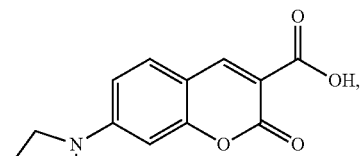
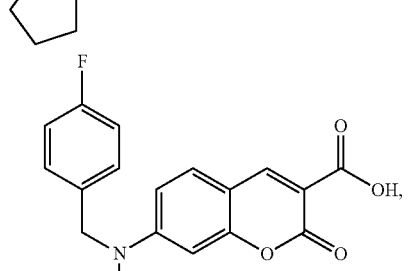
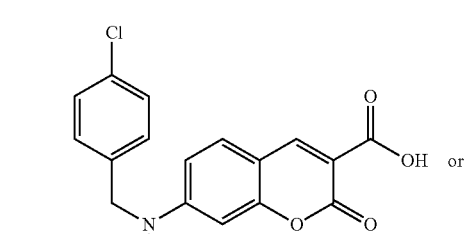 or
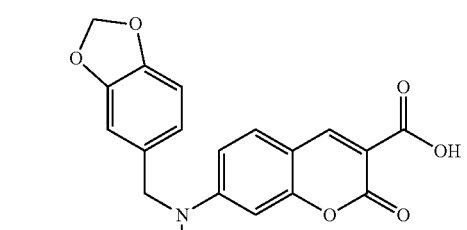
or a salt thereof.

Another specific compound of formula I is:
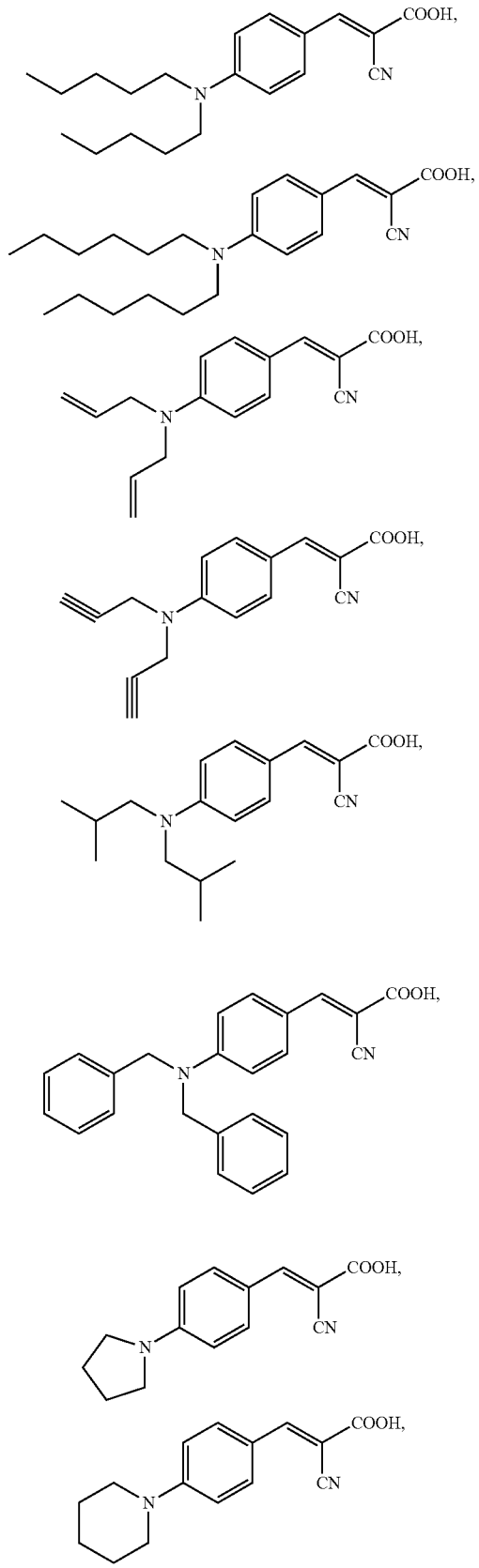
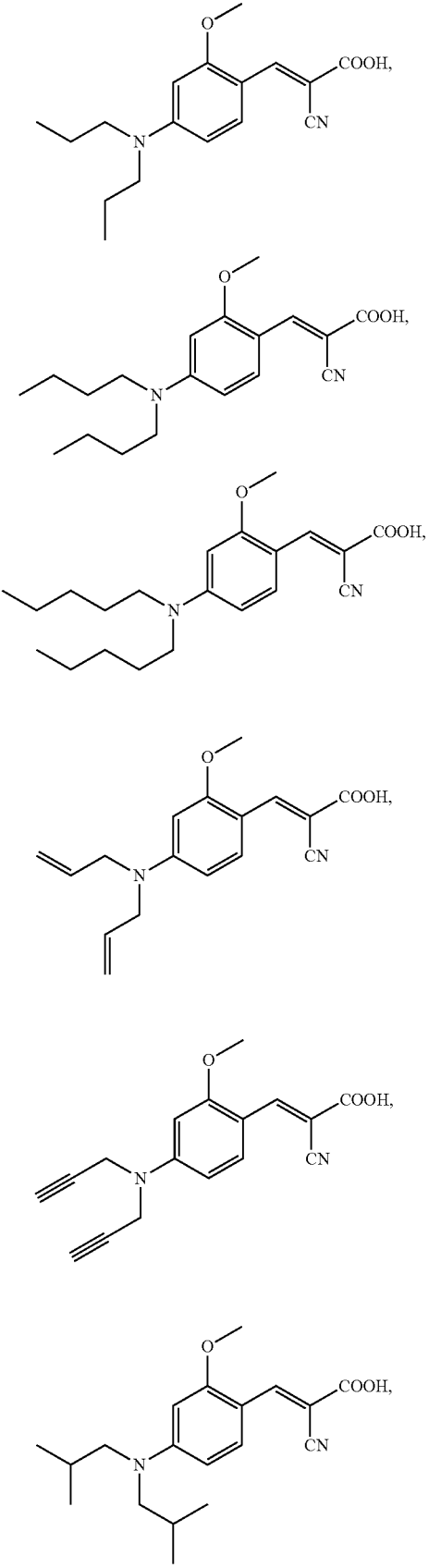

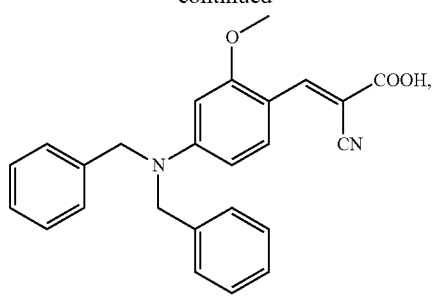
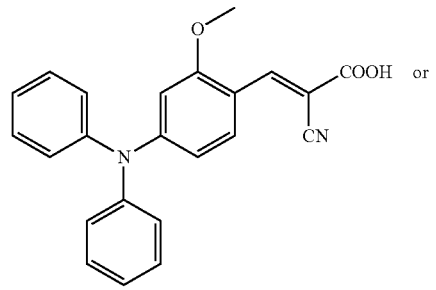 or
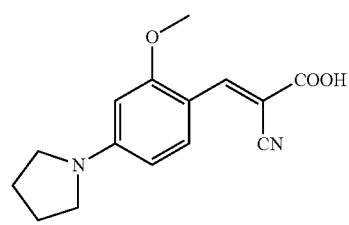
or a salt thereof.
Another specific compound of formula I is:
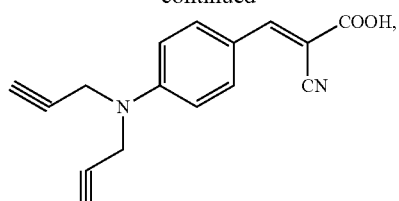
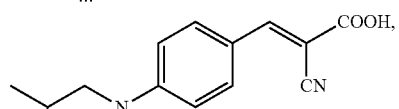
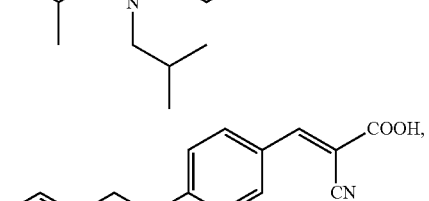
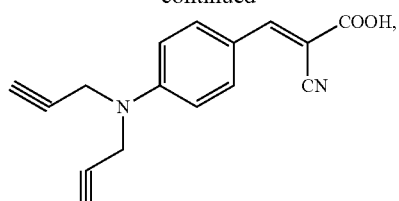
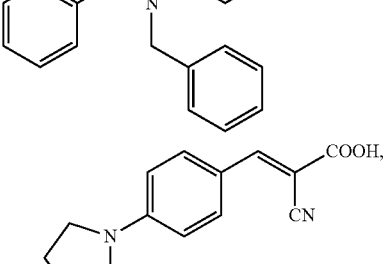
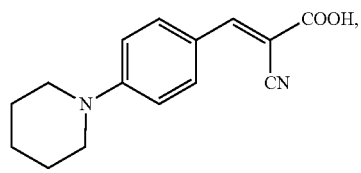
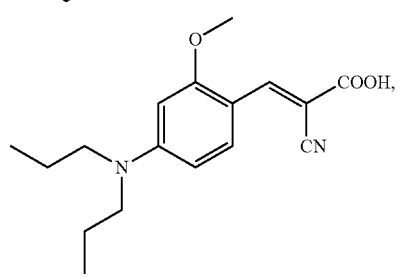
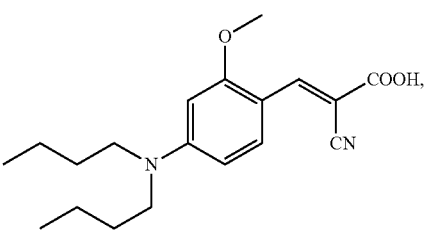
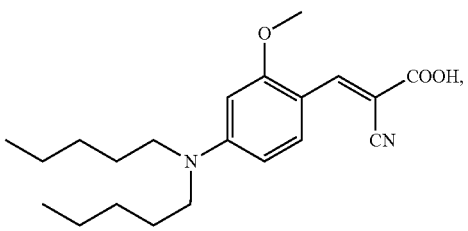 [SMILES: CCCCCN(CCCCC)c1ccc(/C=C(\C#N)C(=O)O)c(OC)c1]

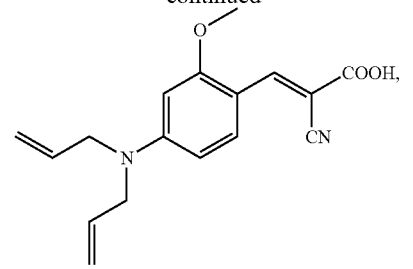
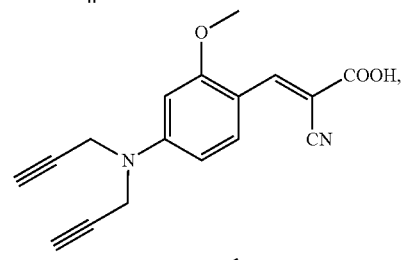
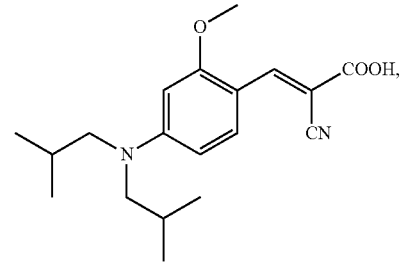
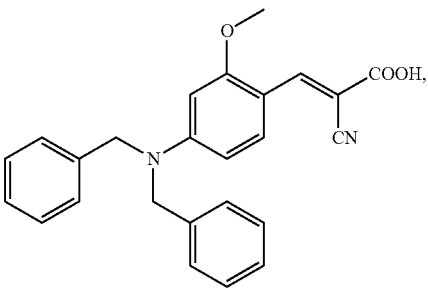 [SMILES: COc1cc(N(Cc2ccccc2)Cc2ccccc2)ccc1/C=C(\C#N)C(=O)O]
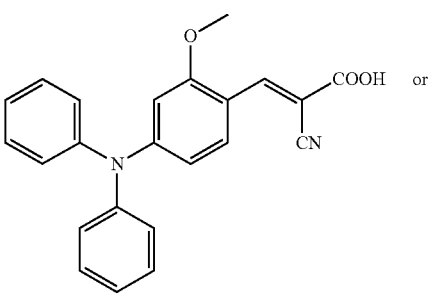
or
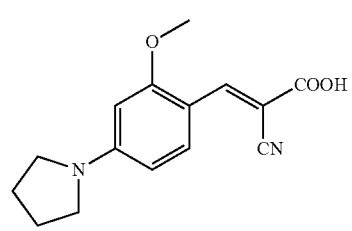 [SMILES: COc1cc(N2CCCC2)ccc1/C=C(\C#N)C(=O)O]
or a salt thereof.
Another specific compound of formula I is:
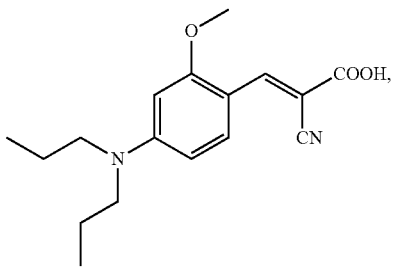
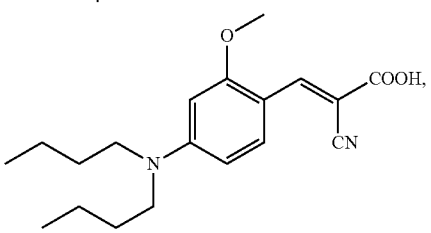
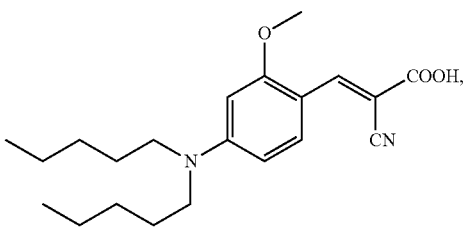
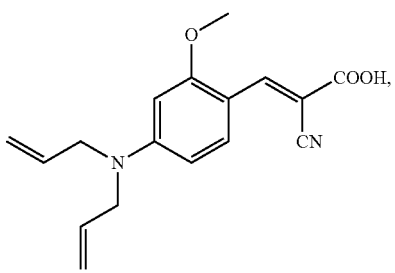
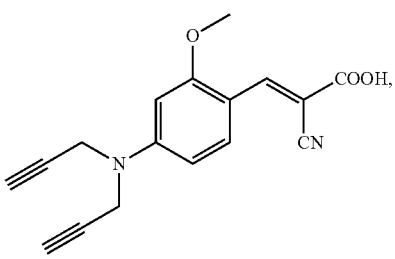
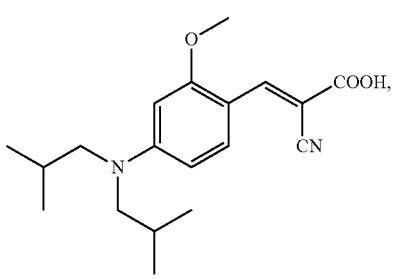

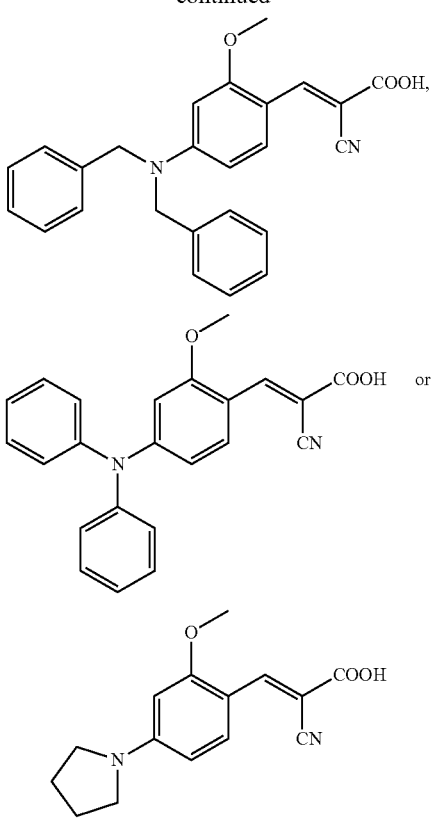
or a salt thereof.
Another specific compound of formula I is:
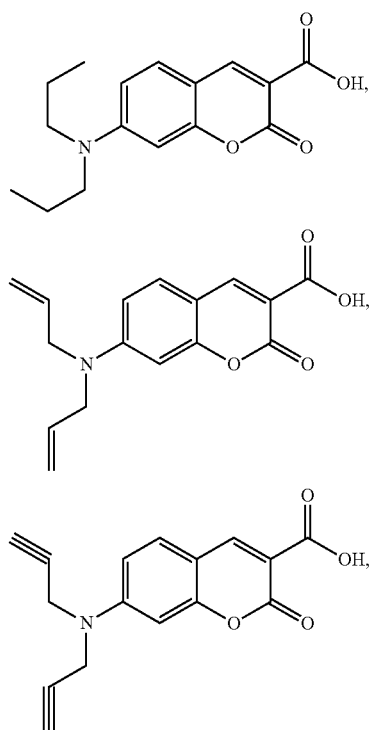
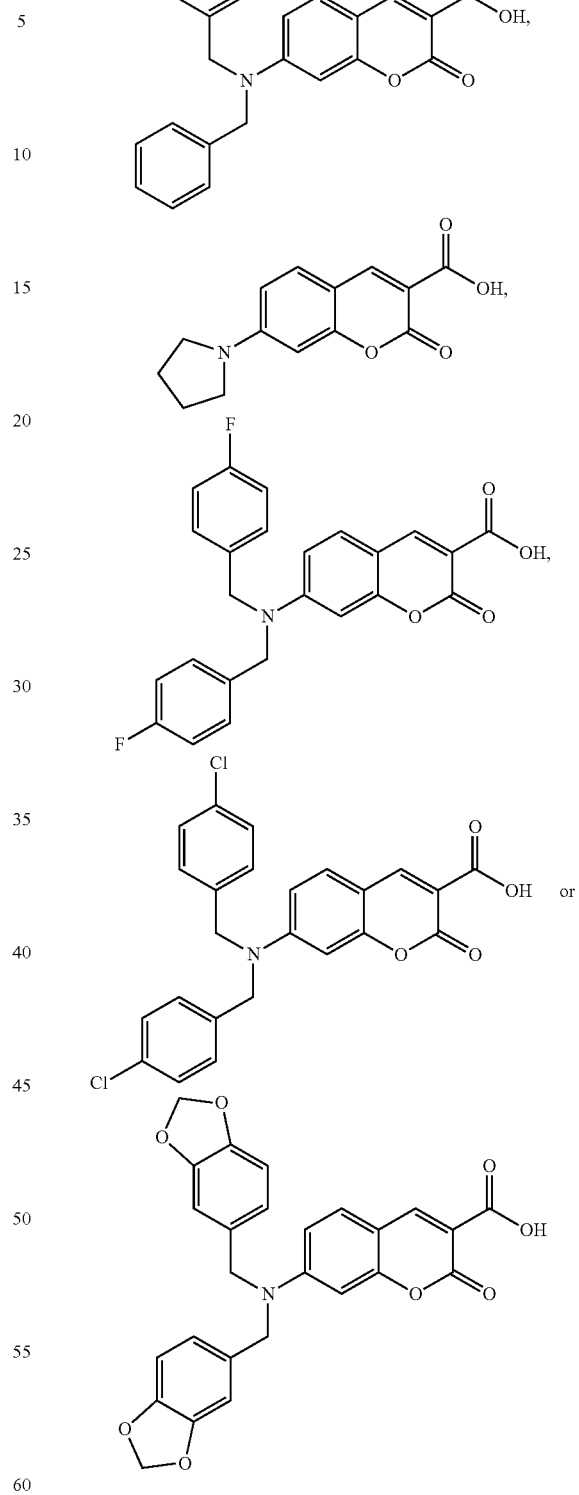
or a salt thereof.
In one embodiment of the invention the compounds of formula I do not include:
(E)-2-cyano-3-(4-(dibutylamino)phenyl)acrylic acid,
(E)-2-cyano-3-(4-(dipropylamino)phenyl)acrylic acid,
(E)-2-cyano-3-(4-(diethylamino)phenyl)acrylic acid, (E)-2-cyano-3-(4-(dimethylamino)phenyl)acrylic acid,
(E)-2-cyano-3-(4-(diethylamino)-2-methylphenyl)acrylic acid,
(E)-2-cyano-3-(4-(diethylamino)-2-methoxyphenyl)acrylic acid,
(E)-2-cyano-3-(4-(diethylamino)-5-methoxy-2-methylphenyl)acrylic acid,
(E)-2-cyano-3-(4-(di-p-tolylamino)phenyl)acrylic acid
(E)-3-(2-acetamido-4-(diethylamino)-5-methoxyphenyl)-2-cyanoacrylic acid,
(E)-2-cyano-3-(4-(dimethylamino)-2-methylphenyl)acrylic acid,
(E)-3-(2-chloro-4-(dimethylamino)phenyl)-2-cyanoacrylic acid,
(E)-3-(4-aminophenyl)-2-cyanoacrylic acid,
(E)-3-(4-((2-chloroethyl)(chloromethyl)amino)phenyl)-2-cyanoacrylic acid,
(E)-3-(4-(bis(2-methoxyethyl)amino)phenyl)-2-cyanoacrylic acid,
(E)-3-(4-(bis(2-chloroethyl)amino)phenyl)-2-cyanoacrylic acid,
(E)-3-(4-((2-chloroethyl)(methyl)amino)phenyl)-2-cyanoacrylic acid,
(E)-2-cyano-3-(4-(diphenylamino)phenyl)acrylic acid,
(E)-3-(4-(bis(4-(dimethylamino)phenyl)amino)phenyl)-2-cyanoacrylic acid,
7-(dimethylamino)-2-oxo-2H-chromene-3-carboxylic acid,
7-(diethylamino)-2-oxo-2H-chromene-3-carboxylic acid,
7-(dibutylamino)-2-oxo-2H-chromene-3-carboxylic acid or
7-(diphenylamino)-2-oxo-2H-chromene-3-carboxylic acid.

In another embodiment of the invention the compounds of formula I do not include:
(E)-2-cyano-3-(4-(dipropylamino)phenyl)acrylic acid,
(E)-2-cyano-3-(4-(diethylamino)phenyl)acrylic acid,
(E)-2-cyano-3-(4-(dimethylamino)phenyl)acrylic acid,
(E)-2-cyano-3-(4-(diethylamino)-2-methylphenyl)acrylic acid,
(E)-2-cyano-3-(4-(diethylamino)-2-methoxyphenyl)acrylic acid,
(E)-2-cyano-3-(4-(diethylamino)-5-methoxy-2-methylphenyl)acrylic acid,
(E)-2-cyano-3-(4-(di-p-tolylamino)phenyl)acrylic acid,
(E)-3-(2-acetamido-4-(diethylamino)-5-methoxyphenyl)-2-cyanoacrylic acid,
(E)-2-cyano-3-(4-(dimethylamino)-2-methylphenyl)acrylic acid,
(E)-3-(2-chloro-4-(dimethylamino)phenyl)-2-cyanoacrylic acid,
(E)-3-(4-aminophenyl)-2-cyanoacrylic acid,
(E)-3-(4-((2-chloroethyl)(chloromethyl)amino)phenyl)-2-cyanoacrylic acid,
(E)-3-(4-(bis(2-methoxyethyl)amino)phenyl)-2-cyanoacrylic acid,
(E)-3-(4-(bis(2-chloroethyl)amino)phenyl)-2-cyanoacrylic acid,
(E)-3-(4-((2-chloroethyl)(methyl)amino)phenyl)-2-cyanoacrylic acid,
(E)-2-cyano-3-(4-(diphenylamino)phenyl)acrylic acid or
(E)-3-(4-(bis(4-(dimethylamino)phenyl)amino)phenyl)-2-cyanoacrylic acid.

In another embodiment of the invention the compounds of formula I do not include:
7-(dimethylamino)-2-oxo-2H-chromene-3-carboxylic acid,
7-(diethylamino)-2-oxo-2H-chromene-3-carboxylic acid,
7-(dibutylamino)-2-oxo-2H-chromene-3-carboxylic acid or
7-(diphenylamino)-2-oxo-2H-chromene-3-carboxylic acid.

In another embodiment of the invention the compounds of formula I do not include:
(E)-2-cyano-3-(4-(dipropylamino)phenyl)acrylic acid,
(E)-2-cyano-3-(4-(diethylamino)phenyl)acrylic acid,
(E)-2-cyano-3-(4-(dimethylamino)phenyl)acrylic acid,
(E)-2-cyano-3-(4-(diethylamino)-2-methylphenyl)acrylic acid,
(E)-2-cyano-3-(4-(diethylamino)-5-methoxy-2-methylphenyl)acrylic acid,
(E)-2-cyano-3-(4-(di-p-tolylamino)phenyl)acrylic acid,
(E)-3-(2-acetamido-4-(diethylamino)-5-methoxyphenyl)-2-cyanoacrylic acid,
(E)-2-cyano-3-(4-(dimethylamino)-2-methylphenyl)acrylic acid,
(E)-3-(2-chloro-4-(dimethylamino)phenyl)-2-cyanoacrylic acid,
(E)-3-(4-aminophenyl)-2-cyanoacrylic acid,
(E)-3-(4-((2-chloroethyl)(chloromethyl)amino)phenyl)-2-cyanoacrylic acid,
(E)-3-(4-(bis(2-methoxyethyl)amino)phenyl)-2-cyanoacrylic acid,
(E)-3-(4-(bis(2-chloroethyl)amino)phenyl)-2-cyanoacrylic acid,
(E)-3-(4-((2-chloroethyl)(methyl)amino)phenyl)-2-cyanoacrylic acid,
(E)-2-cyano-3-(4-(diphenylamino)phenyl)acrylic acid,
(E)-3-(4-(bis(4-(dimethylamino)phenyl)amino)phenyl)-2-cyanoacrylic acid,
7-(dimethylamino)-2-oxo-2H-chromene-3-carboxylic acid,
7-(diethylamino)-2-oxo-2H-chromene-3-carboxylic acid,
7-(dibutylamino)-2-oxo-2H-chromene-3-carboxylic acid or
7-(diphenylamino)-2-oxo-2H-chromene-3-carboxylic acid.

In another embodiment of the invention the compounds of formula I do not include:
(E)-2-cyano-3-(4-(diethylamino)-2-methoxyphenyl)acrylic acid.

Processes for preparing compounds of formula I are provided as further embodiments of the invention and are illustrated in Schemes 1-3 in which the meanings of the generic radicals are as given above unless otherwise qualified. Scheme 1 depicts a general procedure for the synthesis of 2-cyano-phenyl acrylic acid compounds of formula I, Scheme 2 depicts a general procedure for the synthesis of methoxy substituted 2-cyano-phenyl acrylic acid compounds of formula I and Scheme 3 depicts a general procedure for the synthesis of 2-oxo-2H-chromene-3-carboxylic acid compounds of formula I. An intermediate useful for preparing a compound of formula I, is a compound of the formula Ia, 2a or 3a or a salt thereof.

Scheme 1

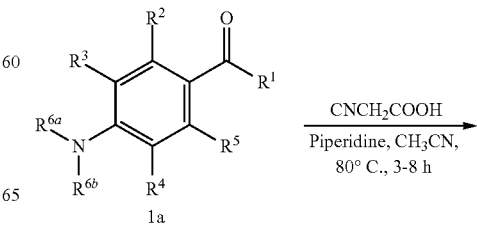

-continued

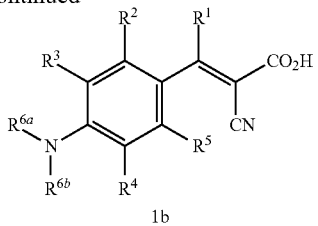

1b

Scheme 2

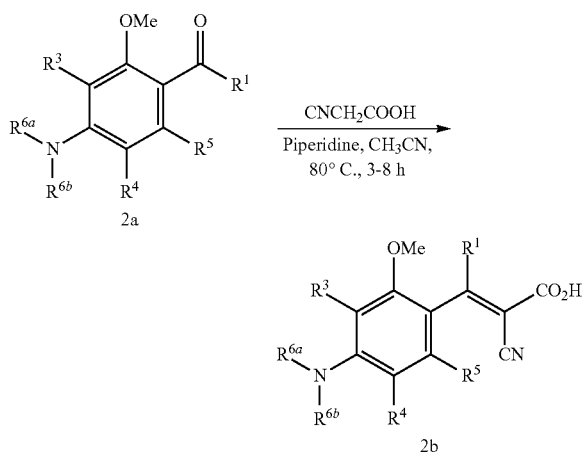

Scheme 3

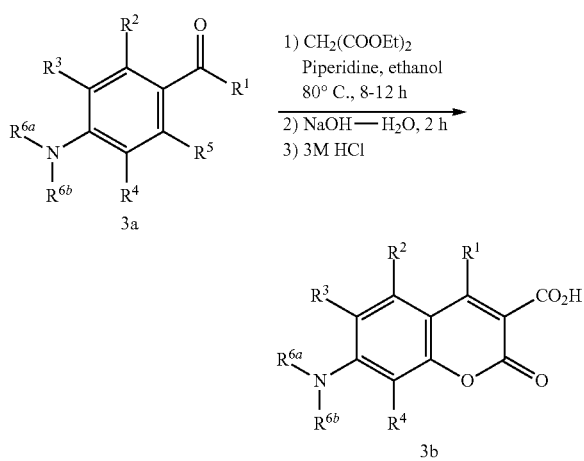

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Aggressive glycolysis is the hallmark of all advanced stage tumors. Accordingly, compounds and compositions described herein may be useful to treat cancers that express MCT's (e.g. lung, breast, brain, prostate, pancreatic, colorectal, ovarian, head and neck).

In addition, compounds and compositions described herein may be useful to prevent organ (e.g. heart, kidney, eye, liver, lung, pancreas, intestine, and thymus) transplant rejection as well as tissues graft (e.g. bone, tendon, cornea, skin, heart valves, and veins) rejection. Compounds and compositions described herein may also be useful for treating autoimmune diseases (e.g. rheumatoid arthritis).

Compounds of the invention can also be administered in combination with other therapeutic agents, for example, other agents that are useful for the treatment of cancer (e.g. lung, breast, brain, prostate, pancreatic, colorectal, ovarian, head and neck cancer) or autoimmune diseases (e.g. rheumatoid arthritis) or agents that are useful for preventing transplant rejection such as organ transplant (e.g. heart, kidney, eye, liver, lung, pancreas, intestine, and thymus) rejection and or tissue graft (e.g. bone, tendon, cornea, skin, heart valve, and vein) rejection. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer or an autoimmune disease or to prevent transplant rejection.

The ability of a compound of the invention to inhibit MCT1 may be determined using pharmacological models which are well known to the art, or using Test A described below.

Test A. MCT1 Inhibition Via Lactate Uptake Rat Brain Endothelial Cells

The entire lactate uptake studies for the inhibition of MCT1 were carried out on RBE4 (Rat Brain Endothelial 4) cells. The expression of MCT1 on these cells was confirmed by Western Blotting. The cells were plated approximately 20-24 hours before the experiment, the number of cells being approximately $10^5$ cells per well. The test compounds were dissolved in DMSO and diluted 1000 times using a solution of HEPES buffer (pH 7.43) which consists of 3 µM $^{14}$C-Lactate and 2 µM L-Lactate. The cells were washed twice with 500 µL of HEPES buffer and the cells were allowed to equilibrate for 15 minutes at 37° C. The HEPES buffer was removed and 250 µL of the test sample was added in triplicates. This was repeated for all the compounds, including the controls (CHC and DMSO). After 15 minutes, the compounds were removed from the well and 500 µL of ice-cold stop buffer (0.1 mM CHC solution in HEPES buffer) was added. The plate was kept on ice. Now, the HEPES buffer in one triplicate was removed and DMSO solution was added and immediately removed and ice-cold stop buffer was added. This was considered as "Zero". One triplicate was left blank, which was used for protein assay after lysing the cells. The cells were washed twice with ice-cold HEPES buffer and then 250 µL of 0.1 M NaOH in 5% Triton-X solution was added and the plate is kept on a shaker for 40 minutes to lyse the cells. 150 µL of the lysed cells was added into 4 mL of the scintillation fluid in a scintillation vial and scintillation count was obtained in disintegrations per minute (dpm). The percent inhibition values were calculated by taking DMSO as minimum. Concentration study (usually 9-12 dilutions) was done to determine the $IC_{50}$ of each compound.

Experimental results from Test A including results for representative compounds of the invention are shown in Table 1. These results demonstrate that compounds of the invention inhibit MCT1. Accordingly compounds of the invention may be useful as therapeutic agents for the treatment of cancer (lung, breast, brain, prostate, pancreatic, colorectal, ovarian, head or neck cancer) or autoimmune diseases (e.g. rheumatoid arthritis) or for preventing transplant rejection (e.g. heart, kidney, eye, liver, lung, pancreas, intestine, or thymus transplant rejection) or for preventing tissue graft rejection (e.g. bone, tendon, cornea, skin, heart valve or vein graft rejection).

Compounds of the inventions may also be useful for diagnosing cancer or cells involved in autoimmune diseases or transplant rejection or tissue graft rejection. The coumarin compounds described herein exhibit fluorescence of excitation ~350 nm and emission ~450 nm. Since rapidly growing cells such as cancer cells and T cells uptake these compounds more than normal cells, the fluorescent MCT1 inhibitors described herein may be useful for imaging cancerous cells or cells involved in an autoimmune response. Additionally, compounds of the invention may be useful as pharmacological tools for the further investigation of cancer function or for the processes involved in an autoimmune response.

TABLE 1

| Compound Number | Compound | $IC_{50}$ (µM) (average) |
|---|---|---|
| 4 | ![structure] | 0.026 |
| 5 | ![structure] | 0.12 |
| 6 | ![structure] | 0.95 |
| 7 | ![structure] | 0.088 |
| 8 | ![structure] | 0.34 |
| 9 | ![structure] | 0.066 |
| 10 | ![structure] | 0.043 |
| 11 | ![structure] | 0.064 |
| 12 | ![structure] | 0.11 |
| 13 | ![structure] | 0.0095 |

TABLE 1-continued
| Compound Number | Compound | IC$_{50}$ (μM) (average) |
|---|---|---|
| 14 | 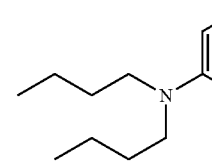 | 0.0076 |
| 15 | | 0.023 |
| 16 | | 0.025 |
| 17 | | 0.091 |
| 18 | | 0.015 |
| 19 | | 0.019 |
| 20 |  | 0.008 |
| 21 | | 0.059 |
| 22 | | 0.299 |
| 23 | | 0.25 |
| 24 | | 0.15 |

TABLE 1-continued

| Compound Number | Compound | IC$_{50}$ (µM) (average) |
|---|---|---|
| 25 | 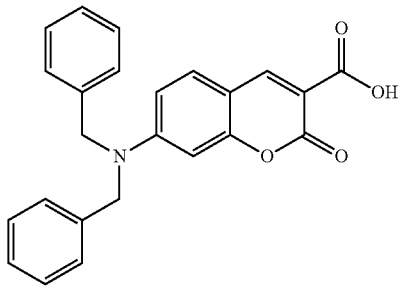 [SMILES: O=C(O)c1cc2ccc(N(Cc3ccccc3)Cc3ccccc3)cc2oc1=O] | 0.048 |
| 26 | 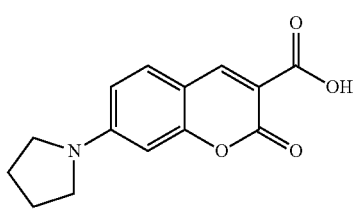 [SMILES: O=C(O)c1cc2ccc(N3CCCC3)cc2oc1=O] | 0.22 |
| 27 | 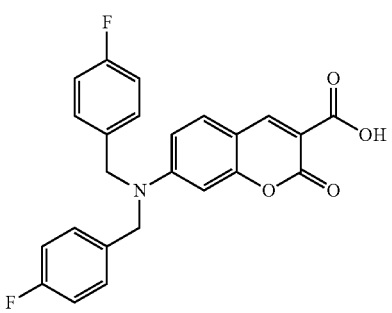 [SMILES: O=C(O)c1cc2ccc(N(Cc3ccc(F)cc3)Cc3ccc(F)cc3)cc2oc1=O] | 0.20 |
| 28 | 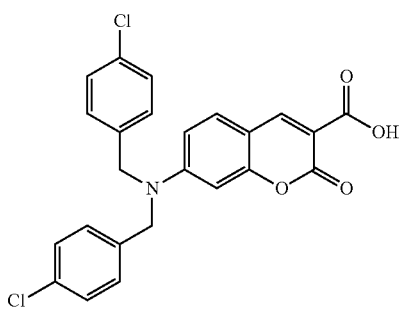 [SMILES: O=C(O)c1cc2ccc(N(Cc3ccc(Cl)cc3)Cc3ccc(Cl)cc3)cc2oc1=O] | 0.92 |
| 29 | 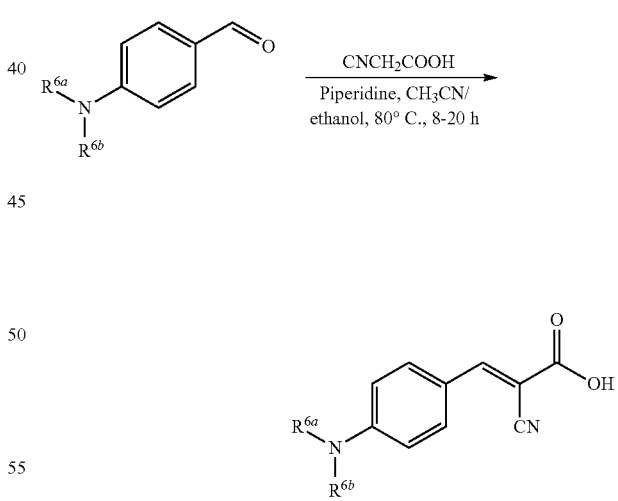 | 0.11 |

The invention will now be illustrated by the following non-limiting Examples.

EXAMPLES

Example 1

Synthesis of Compounds 4-12 (Table I)

To a solution of the substituted benzaldehyde (10 mmol) in 20 ml acetonitrile or ethanol, was added cyanoacetic acid (15 mmol) and piperidine (10 mmol) and refluxed for 3-8 h at 80° C. Upon the completion of the reaction, the above solution was poured into a mixture of 3M HCl (10 mL) in ice. The solution was stirred for 10 to 15 minutes and the solid was filtered using Buchner funnel. The solid was washed with water and acetonitrile. The pure compound was obtained upon recrystallization.

TABLE 2

| Compound Number | Compound | Elemental Calculated | | | Elemental Observed | | | Yield (%) |
|---|---|---|---|---|---|---|---|---|
| | | C % | H % | N % | C % | H % | N % | |
| 4 | dibutylamino phenyl cyanoacrylic acid | 71.97 | 8.05 | 9.33 | 71.83 | 8.38 | 9.35 | 65 |
| 5 | dipentylamino phenyl cyanoacrylic acid | 73.14 | 8.59 | 8.53 | 72.61 | 8.37 | 8.16 | 70 |
| 6 | dihexylamino phenyl cyanoacrylic acid | 74.12 | 9.05 | 7.86 | 74.18 | 9.99 | 7.74 | 68 |
| 7 | diallylamino phenyl cyanoacrylic acid | 71.62 | 6.01 | 10.44 | 70.98 | 6.66 | 11.36 | 60 |
| 8 | dipropargylamino phenyl cyanoacrylic acid | 72.72 | 4.58 | 10.6 | 70.62 | 4.7 | 10.28 | 62 |
| 9 | diisobutylamino phenyl cyanoacrylic acid | 71.97 | 8.05 | 9.33 | 71.48 | 8.49 | 9.23 | 61 |
| 10 | dibenzylamino phenyl cyanoacrylic acid | 78.24 | 5.47 | 7.60 | 77.30 | 5.33 | 7.88 | 72 |

TABLE 2-continued

| Compound Number | Compound | Elemental Calculated C% | H% | N% | Elemental Observed C% | H% | N% | Yield (%) |
|---|---|---|---|---|---|---|---|---|
| 11 | pyrrolidine-phenyl-CH=C(CN)COOH | 69.41 | 5.82 | 11.56 | 68.75 | 5.50 | 11.20 | 68 |
| 12 | piperidine-phenyl-CH=C(CN)COOH | 70.29 | 6.29 | 10.93 | 70.51 | 6.45 | 11.01 | 67 |

Example 2

Synthesis of Compounds 13-21 (Table 3)

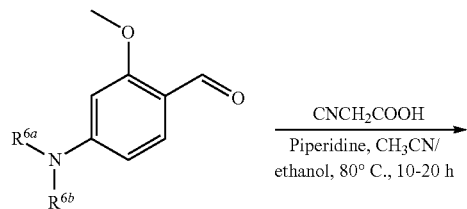

→ CNCH₂COOH / Piperidine, CH₃CN/ethanol, 80° C., 10-20 h →

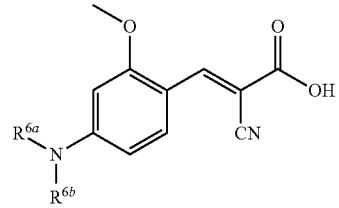

To a solution of the substituted o-methoxy-benzaldehyde (10 mmol) in 20 ml acetonitrile or ethanol was added cyanoacetic acid (15 mmol) and piperidine (10 mmol) and refluxed for 10-20 h at 80° C. Upon the completion of the reaction, the above solution was poured into a mixture of 3 M HCl (10 mL) in ice. The solution was stirred for 10 to 15 minutes and the solid was filtered using Buchner funnel. The solid was washed with water and acetonitrile and the pure compound was obtained upon recrystallization.

TABLE 3

| Compound Number | Compound | Elemental Calculated C% | H% | N% | Elemental Observed C% | H% | N% | Yield (%) |
|---|---|---|---|---|---|---|---|---|
| 13 | dipropylamino-methoxyphenyl-CH=C(CN)COOH | 67.53 | 7.33 | 9.26 | 67.11 | 7.35 | 9.14 | 62 |
| 14 | dibutylamino-methoxyphenyl-CH=C(CN)COOH | 69.06 | 7.93 | 8.48 | 70.01 | 7.66 | 8.56 | 60 |

TABLE 3-continued

| Compound Number | Compound | Elemental Calculated | | | Elemental Observed | | | Yield (%) |
|---|---|---|---|---|---|---|---|---|
| | | C % | H % | N % | C % | H % | N % | |
| 15 | | 70.36 | 8.44 | 7.81 | 70.51 | 8.60 | 7.92 | 74 |
| 16 | | 68.44 | 6.08 | 9.39 | 68.59 | 6.12 | 9.48 | 70 |
| 17 | | 69.38 | 4.79 | 9.52 | 69.89 | 4.99 | 9.78 | 66 |
| 18 | | 69.06 | 7.93 | 8.48 | 68.95 | 7.57 | 8.66 | 58 |
| 19 | | 75.36 | 5.57 | 7.03 | 75.79 | 5.86 | 7.34 | 62 |

TABLE 3-continued

| Compound Number | Compound | Elemental Calculated | | | Elemental Observed | | | Yield (%) |
|---|---|---|---|---|---|---|---|---|
| | | C % | H % | N % | C % | H % | N % | |
| 20 | ![compound 20] | 74.58 | 4.90 | 7.56 | 74.12 | 4.47 | 7.82 | 66 |
| 21 | ![compound 21] | 66.16 | 5.92 | 10.29 | 66.36 | 5.86 | 10.31 | 68 |

Example 3

Synthesis of Compounds 22-29 (Table 4)

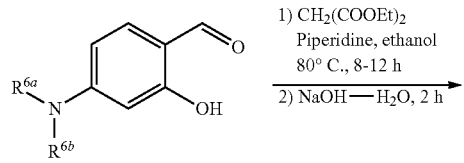

1) CH$_2$(COOEt)$_2$
   Piperidine, ethanol
   80° C., 8-12 h
2) NaOH—H$_2$O, 2 h -continued

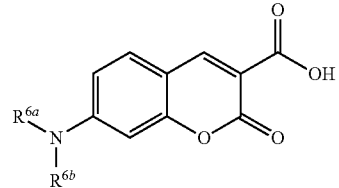

To a solution of substituted o-hydroxy-benzaldehyde (10 mmol) in 20 ml ethanol, was added diethyl malonate (20 mmol) and piperidine (13 mmol) and refluxed for 8-12 h at 80° C. Upon the completion of the reaction, the above solution was evaporated and further refluxed in 10 ml of 10% NaOH solution. The reaction was quenched with 3M HCl and worked up with ethyl acetate. The compound was purified by column chromatography (eluted with 100% ethyl acetate) and recrystallized.

TABLE 4

| Compound Number | Compound | Elemental Calculated | | | Elemental Observed | | | Yield (%) |
|---|---|---|---|---|---|---|---|---|
| | | C % | H % | N % | C % | H % | N % | |
| 22 | | 66.42 | 6.62 | 4.84 | 66.54 | 6.76 | 4.91 | 50 |

TABLE 4-continued

| Compound Number | Compound | Elemental Calculated | | | Elemental Observed | | | Yield (%) |
|---|---|---|---|---|---|---|---|---|
| | | C % | H % | N % | C % | H % | N % | |
| 23 | 7-(diallylamino)-2-oxo-2H-chromene-3-carboxylic acid | 67.36 | 5.30 | 4.91 | 67.38 | 5.19 | 4.98 | 64 |
| 24 | 7-(di(prop-2-yn-1-yl)amino)-2-oxo-2H-chromene-3-carboxylic acid | 68.32 | 3.94 | 4.98 | 68.39 | 3.97 | 4.86 | 53 |
| 25 | 7-(dibenzylamino)-2-oxo-2H-chromene-3-carboxylic acid | 74.79 | 4.97 | 3.63 | 74.87 | 4.56 | 3.84 | 58 |
| 26 | 2-oxo-7-(pyrrolidin-1-yl)-2H-chromene-3-carboxylic acid | 64.86 | 5.05 | 5.40 | 64.21 | 4.87 | 5.12 | 59 |
| 27 | 7-(bis(4-fluorobenzyl)amino)-2-oxo-2H-chromene-3-carboxylic acid | 68.41 | 4.07 | 3.32 | 68.66 | 4.34 | 3.38 | 55 |

TABLE 4-continued

| Compound Number | Compound | Elemental Calculated | | | Elemental Observed | | | Yield (%) |
|---|---|---|---|---|---|---|---|---|
| | | C % | H % | N % | C % | H % | N % | |
| 28 | 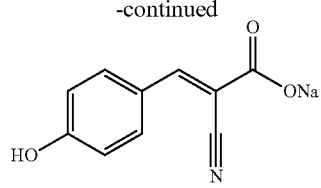 | 63.45 | 3.77 | 3.08 | 63.55 | 3.84 | 2.97 | 57 |
| 29 | | 65.96 | 4.05 | 2.96 | 65.87 | 3.87 | 3.08 | 55 |

Example 4

Toxicity Study in Healthy ICR Mice

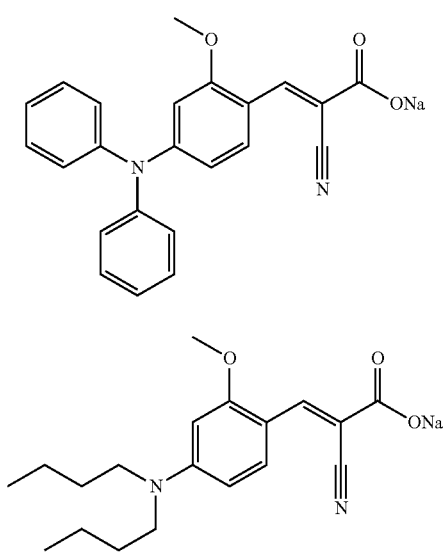

CHC

Protocol

60 ICR mice weighing ~27 grams were randomly assigned into 5 groups (12 animals, 6 male and 6 female per group), one group being the control group without any drug administration (food only). The drugs were administered twice daily by P.O. or I.P. Group 1 and 3 were administered orally with 50 mg/Kg of Compound 20 and 18 mg/Kg of Compound 14 respectively. Group 2 and 4 mice were injected intraperitoneally with 6.67 mg/Kg of Compound 20 and 5.3 mg/Kg of Compound 14 (dissolved in water) respectively. The body weights of mice were recorded daily for 22 days. At the end of the $22^{nd}$ day, 3 mice were randomly selected from each group and their blood samples were collected for detailed analysis of white blood cell (WBC) and red blood cell (RBC) counts. The mice were then euthanized with $CO_2$.

Results

TABLE 1

Body Weight Changes of
ICR Mice in Compound 20 and Compound 14 Toxicity Study

| Group | Weight in grams (Day 0) | Weight in grams (Day 22) |
|---|---|---|
| Compound 20 (50 mg/kg, p.o.) | 26.91 | 32.61 |
| Compound 20 (6.67 mg/kg, i.p) | 26.98 | 33.54 |
| Compound 14 (18 mg/kg, p.o) | 27.04 | 32.60 |
| Compound 14 (5.3 mg/kg, i.p) | 27.05 | 32.53 |
| No treatment | 27.03 | 35.28 |

TABLE 2

WBC Count in Toxicity Study of ICR Mice

| | Compound 20 (50 mg/kg, p.o) | Compound 20 (6.67 mg/kg, i.p) | Compound 14 (18 mg/kg, p.o) | Compound 14 (5.3 mg/kg, i.p) | No treatment |
|---|---|---|---|---|---|
| WBC ± SEM ($10^{10}$/L) | 4.10 ± 0.3 | 3.83 ± 0.38 | 4.57 ± 0.49 | 5.80 ± 0.72 | 2.97 ± 0.23 |

TABLE 3

RBC Count in Toxicity Study of ICR Mice

| | Compound 20 (50 mg/kg, p.o) | Compound 20 (6.67 mg/kg, i.p) | Compound 14 (18 mg/kg, p.o) | Compound 14 (5.3 mg/kg, i.p) | No treatment |
|---|---|---|---|---|---|
| RBC ± SEM ($10^{13}$/L) | 1.75 ± 0.06 | 1.82 ± 0.05 | 1.58 ± 0.02 | 1.58 ± 0.05 | 1.62 ± 0.09 |

Inference

From this preliminary study, it can be inferred that potent MCT1 inhibitors do not cause systemic toxicity and are well tolerated in healthy ICR mice.

Example 5

Toxicity Study in BALB/C Nude Mice Containing WiDr Colorectal Adenocarcinoma Xenograft Protocol Female BALB/c nude mice weighing ~20 g were taken and 5.0 10$^6$ WiDr cancer cells were implanted into their right flanks with a 1:1 mixture of 0.1 mL PBS and matrigel. The tumor was allowed to grow to a size of ~150 cubic millimeters (14 days). The mice were randomly chosen by chance and assigned into 5 groups (6 mice per group), one group being the control group to which tumor was allowed to grow without any drug administration (food only). The drugs were administered twice daily by P.O. or I.P. Group 1 mice were administered orally with 50 mg/kg of Compound 20. Groups 2, 3 and 4 mice were treated via IP with 10 mg/kg Compound 20, 8 mg/kg of Compound 14 and 238 mg/kg CHC respectively. Body weight changes were recorded every two days for 3 weeks.

Results

TABLE 3

The Body Weight Changes in BALB/C Nude Mice in Toxicity Study of Compound 20 and Compound 14

| Group | Weight in grams (Day 0) | Weight in grams (Day 22) |
|---|---|---|
| Compound 20 (50 mg/kg, p.o.) | 21.85 | 23.01 |
| Compound 20 (10 mg/kg, i.p.) | 21.93 | 23.38 |
| Compound 14 (8 mg/kg, i.p.) | 22.08 | 23.50 |
| No treatment | 22.10 | 24.21 |

Inference

From this study also, it can be inferred that MCT1 inhibitors do not cause systemic toxicity and are well tolerated in nude mice.

Example 6

Pharmacokinetic Study of Compound 20 in ICR Mice

Protocol:

60 male ICR mice were split into two groups of 30. In each group the mice were prescribed Compound 20 at a dosage of 100 mg/kg. This dose was administered orally in group 1 and intraperitoneally in group 2. Each group of 30 mice was subdivided into groups of 3 mice. Blood samples were taken through orbital sinus method at 0, 0.083, 0.25, 0.5, 1, 2, 4, 6, 8 and 24 hours after administering Compound 20 and taken into tubes with anticoagulant at room temperature at least 30 minutes prior to centrifugation, then centrifuged at 10000 rpm for 5 minutes at 4° C. to separate plasma from the blood samples. Following centrifugation, the resulting serum was transferred to clean tubes and stored frozen at −80° C. Immediately following the blood samples, the brain tissue samples of mice were removed and stored frozen at −80° C.

A 20% brain homogenate was prepared by weighing brain tissue sample and adding, corresponding volume of saline into the manual homogenator. The dilution factor was 5 (w/v=1 g: 4 mL). The brain tissue sample was grinded slowly and repeatedly until it has become homogenous.

Plasma and Brain samples were centrifuged at 15777×g for 5 minutes, and 180 ul of supernatant was placed in a 96-well assay plate. To each well, 200 ul of a 50% ACN/H$_2$O was added and the plates were shake-mixed for 3 minutes. 5 ul aliquots of each well were then analyzed using LC-MS/MS.

The standard non-compartmental model was used to generate the pharmacokinetic parameters: $C_{max}$, $T_{max}$, $t_{1/2}$, $AUC_{0->last}$, $AUC_{0->inf}$, CL/F, and Vz/F. The maximum plasma concentration, $C_{max}$, and its corresponding time, $T_{max}$ were directly recorded. Elimination rate constant $k_{el}$ was determined by linear regression of the terminal points of the semi-log plot of concentration against time. Elimination half-life was calculated by the formula; $t_{1/2}=0.693/k_{el}$. The Area Under the curve value from time 0 to 24 hours was defined as $AUC_{t->last}$ and calculated using the linear trapezoidal rule.

Results:

Table 4 illustrates the individual and mean plasma concentration data (ng/mL) for Compound 20 after intragastrical administration to mice.

TABLE 4

| Time (h) | Plasma Concentration (ng/ml) p.o. (n = 3) | | | | |
| --- | --- | --- | --- | --- | --- |
| | 1# | 2# | 3# | Mean | SD |
| 0 | 0 | 0 | 0 | 0 | 0 |
| 0.083 | 2210 | 4050 | 4040 | 3433 | 1059 |
| 0.25 | 9690 | 11300 | 6400 | 9130 | 2498 |
| 0.5 | 19100 | 20700 | 6580 | 15460 | 7732 |
| 1 | 3610 | 4830 | 12700 | 7047 | 4934 |
| 2 | 3270 | 1380 | 4790 | 3147 | 1708 |
| 4 | 2880 | 5160 | 1240 | 3093 | 1969 |
| 6 | 1470 | 2230 | 3720 | 2473 | 1145 |
| 8 | 5780 | 2370 | 3880 | 4010 | 1709 |
| 24 | 111 | 19.3 | 12.8 | 47.7 | 54.9 |

Table 5 illustrates individual and mean plasma concentration data (ng/mL) for Compound 20 after intraperitoneal administration to mice.

TABLE 5

| Time (h) | Plasma Concentration (ng/ml) i.p. (n = 3) | | | | |
| --- | --- | --- | --- | --- | --- |
| | 1# | 2# | 3# | Mean | SD |
| 0 | 0 | 0 | 0 | 0 | 0 |
| 0.083 | 18800 | 33300 | 40400 | 30833 | 11009 |
| 0.25 | 78300 | 29400 | 60100 | 55933 | 24715 |
| 0.5 | 51400 | 30400 | 30200 | 37333 | 12183 |
| 1 | 31800 | 45600 | 26900 | 34767 | 9697 |
| 2 | 38800 | 27800 | 38900 | 35167 | 6380 |
| 4 | 25000 | 24000 | 26400 | 25133 | 1206 |
| 6 | 14200 | 3980 | 5360 | 7847 | 5545 |
| 8 | 2760 | 3160 | 2590 | 2837 | 293 |
| 24 | 41.8 | 249 | 70.9 | 121 | 112 |

Table 6 illustrates mean pharmacokinetic parameters of Compound 20 in mice,

TABLE 6

| | | PK parameters (Mean ± SD) | | | | | | |
| --- | --- | --- | --- | --- | --- | --- | --- | --- |
| Dose route | | $AUC_{0-last}$ (µg/L * h) | $AUC_{0-\infty}$ (µg/L * h) | $t_{1/2Z}$ (h) | $T_{max}$ (h) | Vz/F (L/kg) | CLz/F (L/h/kg) | $C_{max}$ (µg/L) |
| p.o. | Mean | 65740 | 66011 | 3.03 | 0.667 | 6.55 | 1.56 | 17500 |
| | SD | 13050 | 13365 | 1.26 | 0.289 | 1.81 | 0.322 | 4233 |
| i.p. | Mean | 200796 | 201474 | 3.19 | 0.5 | 2.35 | 0.499 | 61333 |
| | SD | 20459 | 19835 | 1.16 | 0.433 | 1.04 | 0.0473 | 16385 | where $AUC_{0-last}$ is area under the plasma concentration-time curve from time zero to time of last measurable concentration, $AUC_{0-\infty}$ is area under the plasma concentration-time curve from time zero to infinity, $T_{max}$ is time to reach maximum (peak) plasma concentration following drug administration, $T_{1/2}$ is biological half-life of the drug, Vz/F is the distribution of a drug between plasma and the rest of the body following oral administration, CLz/F is apparent total body clearance of the drug from plasma and $C_{max}$ is maximum (peak) plasma drug concentration.

Inference

From this study, it can be inferred that pharmacokinetics parameters for representative Compound 20 are satisfactory.

Example 7

Anticancer Efficacy in Balb/c Nude Mice

Protocol

Female BALB/c nude mice weighing ~20 g were taken and $5.0 \; 10^6$ WiDr cancer cells were implanted into their right flanks with a 1:1 mixture of 0.1 mL PBS and matrigel. The tumor was allowed to grow to a size of ~150 cubic millimeters (2 weeks). The mice were randomly chosen by chance and assigned into 5 groups (6 animals/group), one group being the control group to which tumor was allowed to grow without any drug administration (food only). The drugs were administered twice daily by P.O. or I.P. Group 1 mice were administered orally with 50 mg/kg of Compound 20. The remaining mice Groups 2, 3 and 4 were treated via IP with 10 mg/kg Compound 20, 8 mg/kg of Compound 14 and 238 mg/kg Compound CHC respectively. The tumor volume was recorded every two days using the formula $$V = \frac{1}{2} \times a \times b^2$$

where 'a' is the long diameter of the tumor and 'b' is the short diameter of the tumor. At the end of the $21^{St}$ day, the mice were euthanized with $CO_2$ and tumor masses were isolated and weighed. The inhibition rate was determined using the formula:

$$\% \text{ inhibition} = \frac{(C - T)}{C} \times 100$$

where C is average tumor weight of control group, T is average tumor weight of test group.

Figure 2:
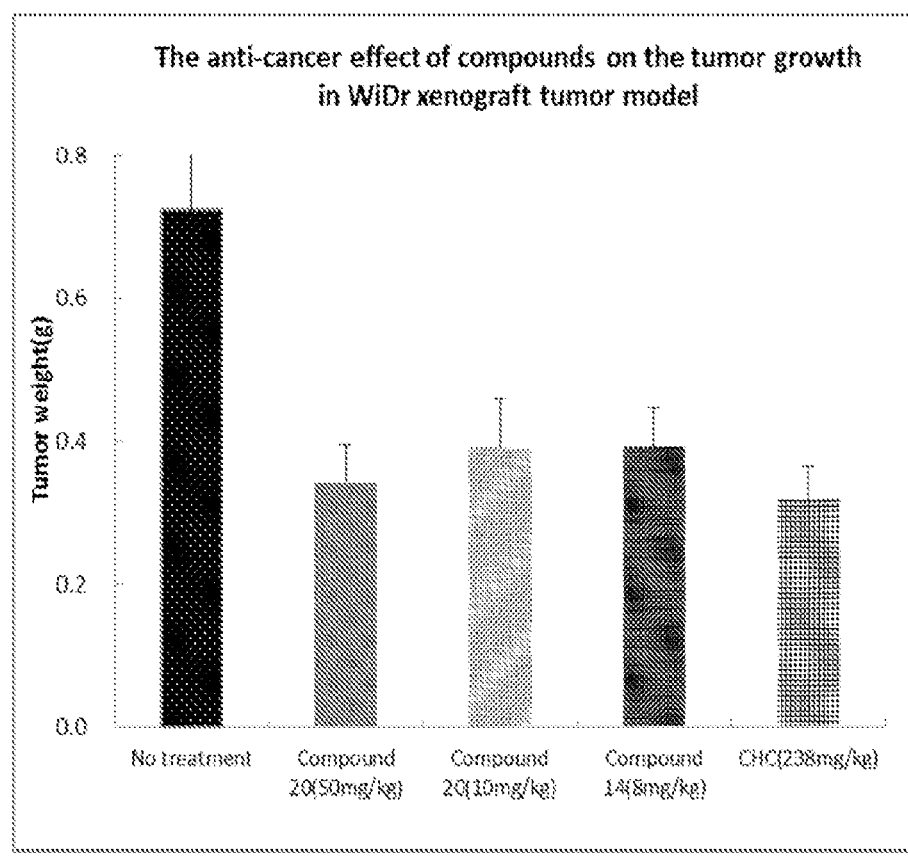
FIG. 2 illustrates the anti-cancer effect of Compound 20, and Compound 14 on the tumor growth in WiDr xenograft tumor model from Example 7.

Results:

The anti-cancer effects of Compound 20, Compound 14, and Compound CHC on the tumor growth in WiDr xenograft tumor model in Example 6 are shown in FIGS. 1 and 2.

Example 8

Anticancer Efficacy in Balb/c Nude Mice

Protocol:

Female BALB/c nude mice weighing ~20 g were taken and $5.0 \times 10^6$ WiDr cancer cells were implanted into their right flanks with 1:1 mixture of 0.1 mL PBS and matrigel. The mice were arbitrarily chosen by chance and assigned into 7 groups (6 animals/group) and the treatment was started from the same day of the implantation of cancer cells. Mice in group 1 were orally administered two times daily with 100 mg/Kg of Compound 20. Mice in group 2 were orally administered four times per day with 50 mg/Kg of Compound 20. Group 3 mice were injected intraperitoneally 2 times per day with 100 mg/Kg of Compound 20. Group 4 mice were injected intraperitoneally one time per day with 100 mg/Kg and group 5 mice were injected intraperitoneally 2 times per day with 50 mg/Kg of Compound 20. Group 6 was treated with 0.2 mL of 2% DMSO in water intraperitoneally 4 times daily and group 7 mice were assigned as the control group to which tumor was allowed to grow without any drug administration (food only). The tumor volume was recorded every two days using the formula $$V = \frac{1}{2} \times a \times b^2$$

where a is the long diameter of the tumor and b is the short diameter of the tumor. At the end of the $14^{th}$ day, the mice from group 1, 2, 3, 4 and 6 were euthanized with $CO_2$ and tumor masses were isolated and weighed. The inhibition rate was determined using the formula:

$$\% \text{ inhibition} = \frac{(C-T)}{C} \times 100$$

where C is average tumor weight of control group, T is average tumor weight of test group. The mice from group 5 and 7 were treated with the above mentioned dosage for one more week (21 days) and were euthanized with $CO_2$ and tumor masses were isolated and weighed. The inhibition rate was determined using the above formula.

Figure 3:
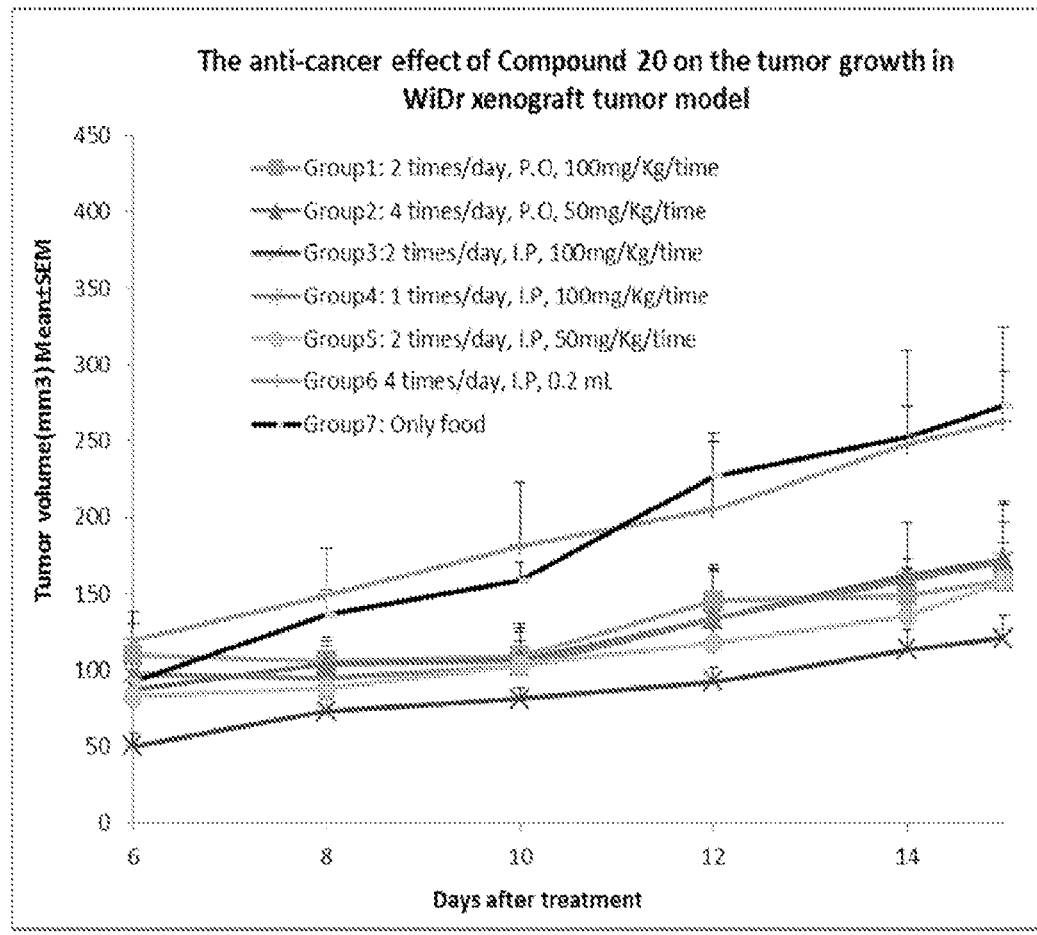
FIG. 3 illustrates the Anti-Cancer Effect of Compound 20 on the Tumor Growth in the WiDr xenograft tumor model (after 14 Days) from Example 8.

Results:

The anti-cancer effect of Compound 20 on the tumor growth in WiDr xenograft tumor model (After 14 Days) from Example 8 are shown in FIG. 3.

Figure 4:
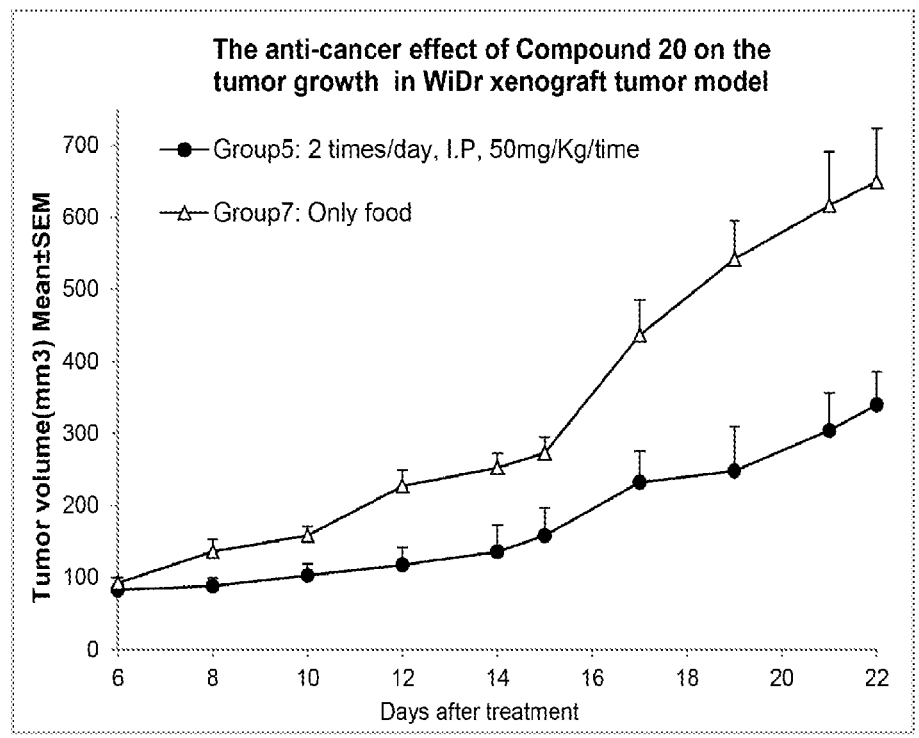
FIG. 4 illustrates the anti-cancer effect of Compound 20 on the tumor growth in the WiDr xenograft tumor model (after 22 Days) from Example 8.

The anti-cancer effect of Compound 20 on the tumor growth in WiDr xenograft tumor model (After 22 Days) from Example 8 are shown in FIG. 4.

Figure 5:
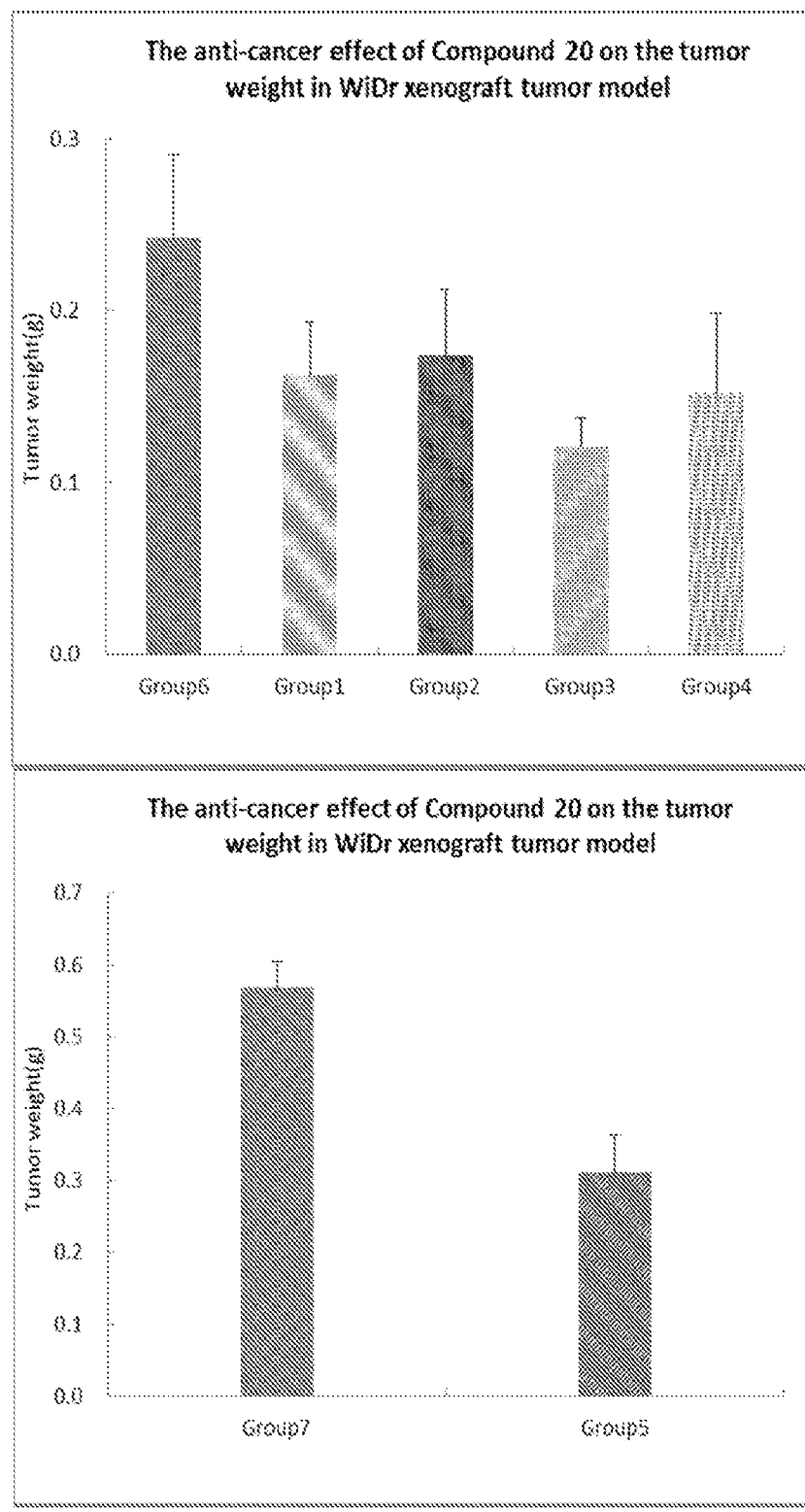
FIG. 5 illustrates the anti-cancer effect of Compound 20 on the tumor weight in the WiDr xenograft tumor model from Example 8.

The anti-cancer effect of Compound 20 on the tumor growth in WiDr xenograft tumor model from Example 8 are shown in FIG. 5.

Figure 6:
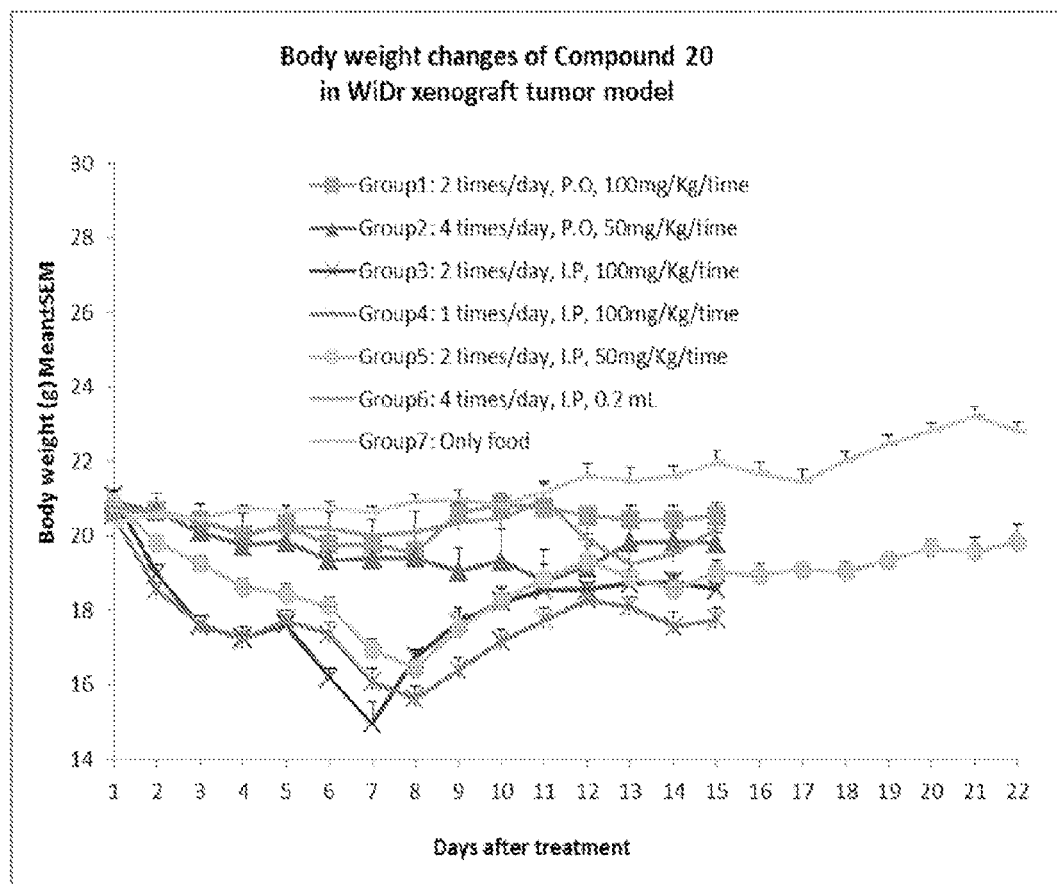
FIG. 6 illustrates the body weight changes in mice from Example 8.

The body weight changes in mice from Example 8 are shown in FIG. 6.

Inference

From this data, it can be inferred that Compound 20 can also be used as an adjuvant therapy without much systemic toxicity.

Example 9

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of the formula:
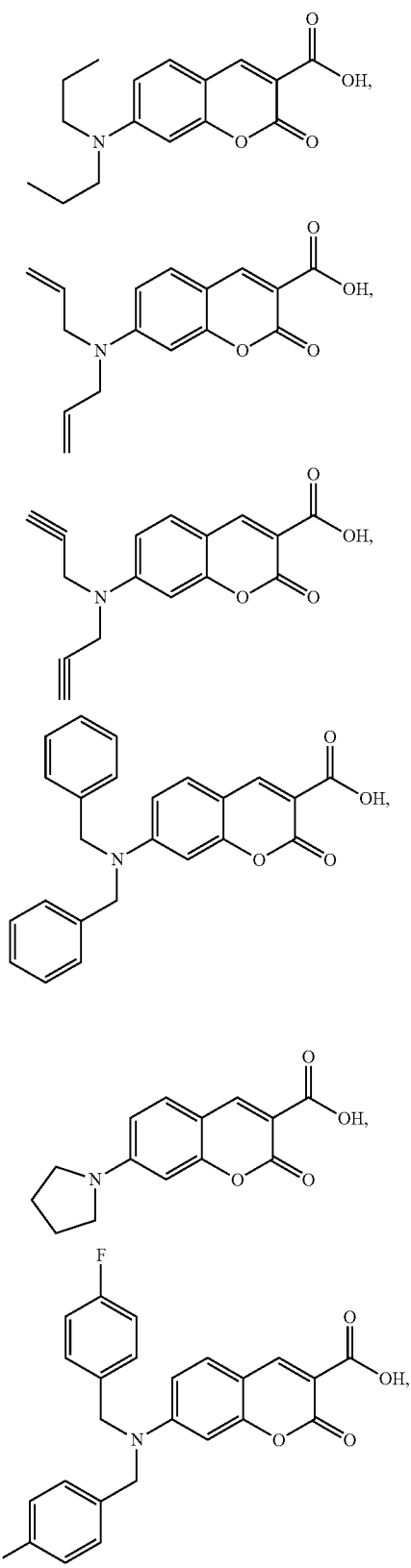
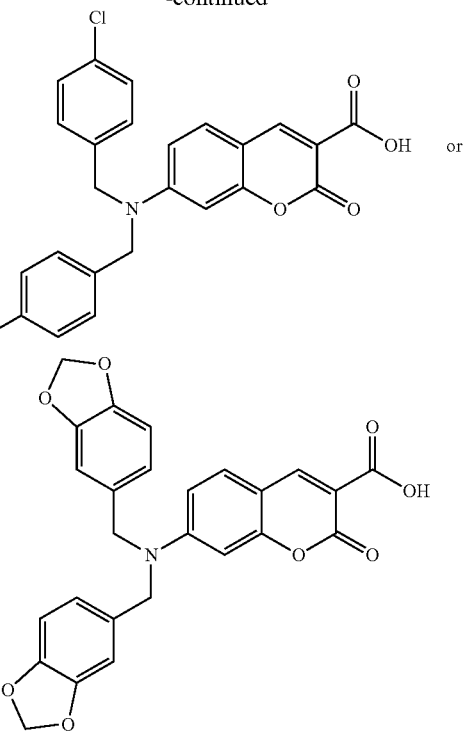
or a salt thereof.
2. The compound of claim 1 which is:
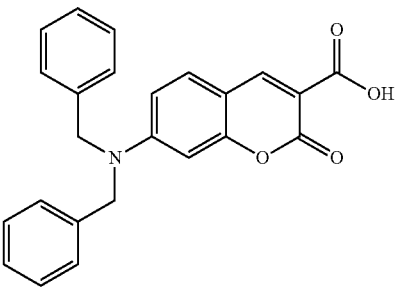 [SMILES: O=C(O)c1cc2ccc(N(Cc3ccccc3)Cc3ccccc3)cc2oc1=O]
or a salt thereof.
3. The compound of claim 1 which is:
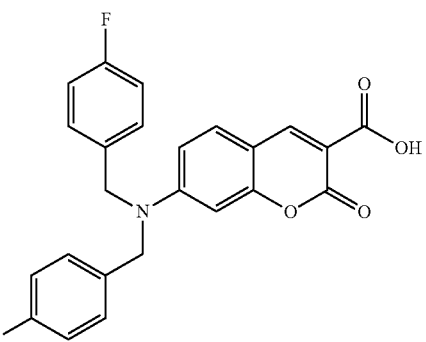
or a salt thereof.

4. The compound of claim 1 which is:
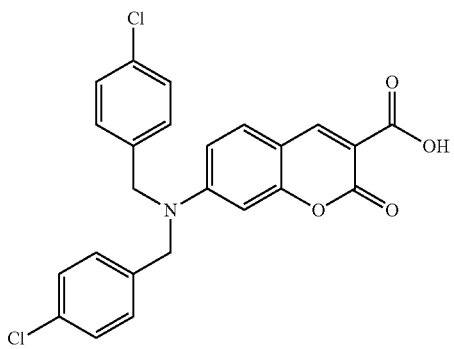 [SMILES: O=C(O)c1cc2ccc(N(Cc3ccc(Cl)cc3)Cc3ccc(Cl)cc3)cc2oc1=O]
or a salt thereof.
5. The compound of claim 1 which is:
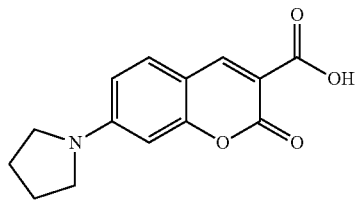 [SMILES: O=C(O)c1cc2ccc(N3CCCC3)cc2oc1=O]
or a salt thereof.
6. The compound of claim 1 which is:
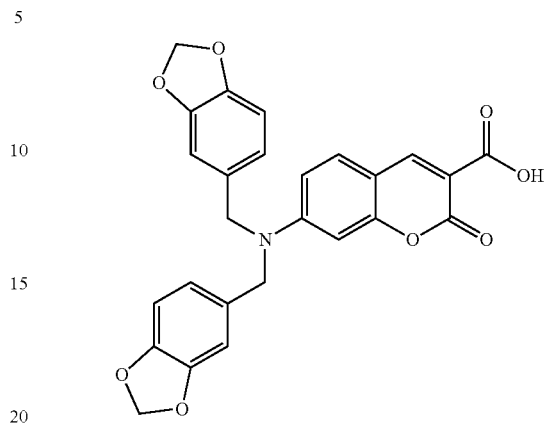
or a salt thereof.
7. A composition comprising a compound of formula Ic as described in claim 1, or a pharmaceutically acceptable salt thereof, and a pharmaceutically acceptable diluent or carrier.
* * * * *

UNITED STATES PATENT AND TRADEMARK OFFICE
CERTIFICATE OF CORRECTION

PATENT NO. : 9,296,728 B2
APPLICATION NO. : 14/373615
DATED : March 29, 2016
INVENTOR(S) : Venkatram R Mereddy et al.

It is certified that error appears in the above-identified patent and that said Letters Patent is hereby corrected as shown below:

On the Title Page

In References Cited, Item (56), Other Publications, please delete "*Transplantation* 84 (2)," and insert -- *Transplantation* 84 (9) --;

In the Abstract, Item (57), please delete "The invention provides compounds of formula (I) or a salt thereof as described herein." and insert -- "The invention provides compounds of formula (I):

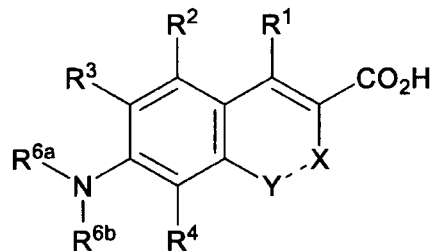

or a salt thereof as described herein. --;

In the Claims

Column 60, Line 27, Claim 7, please delete "of formula Ic" therefor.

Signed and Sealed this
Twenty-third Day of May, 2017

Michelle K. Lee
*Director of the United States Patent and Trademark Office*

UNITED STATES PATENT AND TRADEMARK OFFICE
CERTIFICATE OF CORRECTION

PATENT NO. : 9,296,728 B2
APPLICATION NO. : 14/373615
DATED : March 29, 2016
INVENTOR(S) : Venkatram R Mereddy et al.

Page 1 of 1

It is certified that error appears in the above-identified patent and that said Letters Patent is hereby corrected as shown below:

In the Specification

In Column 1 Line 2 insert:
-- STATEMENT REGARDING FEDERALLY SPONSORED RESEARCH
This invention was made with government support under W81XWH-15-1-0047 awarded by USDOD-ARMY/MRMC. The government has certain rights in the invention. -- therefor.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*